(12) United States Patent
Watanabe et al.

(10) Patent No.: US 7,985,383 B2
(45) Date of Patent: Jul. 26, 2011

(54) ENDOSCOPE STERILIZING TEST PACK

(75) Inventors: Atsushi Watanabe, Tokyo (JP); Tsuruo Hatori, Kanagawa (JP); Akihisa Ogawa, Tokyo (JP)

(73) Assignees: Olympus Medical Systems Corp. (JP); Olympus Corporation (JP)

( * ) Notice: Subject to any disclaimer, the term of this patent is extended or adjusted under 35 U.S.C. 154(b) by 1165 days.

(21) Appl. No.: 11/483,375

(22) Filed: Jul. 7, 2006

(65) Prior Publication Data

US 2006/0263245 A1 Nov. 23, 2006

Related U.S. Application Data

(63) Continuation of application No. PCT/JP2005/000196, filed on Jan. 11, 2005.

(30) Foreign Application Priority Data

Jan. 8, 2004 (JP) ................................. 2004-003505
Dec. 28, 2004 (JP) ................................. 2004-382118

(51) Int. Cl.
*G01N 21/75* (2006.01)
*A61L 2/28* (2006.01)
*A61L 2/00* (2006.01)
*A61B 1/00* (2006.01)

(52) U.S. Cl. .......... 422/401; 422/400; 422/402; 422/28; 422/33; 422/119; 422/297; 422/300; 600/101; 600/133

(58) Field of Classification Search ........................ None
See application file for complete search history.

(56) References Cited

U.S. PATENT DOCUMENTS

| 4,943,414 A * | 7/1990 | Jacobs et al. ..................... 422/28 |
| 5,872,004 A | 2/1999 | Bolsen |
| 2003/0087441 A1 | 5/2003 | Lemus et al. ..................... 436/1 |
| 2003/0215923 A1* | 11/2003 | Witcher et al. ............... 435/71.1 |

FOREIGN PATENT DOCUMENTS

| CA | 2019504 | 5/1991 |
| DE | 87 00 471 U1 | 3/1987 |
| EP | 0 628 814 | 12/1994 |
| EP | 1 698 354 | 9/2006 |
| JP | 3-159650 | 7/1991 |
| JP | 05-253277 | 10/1993 |
| JP | 2001-526399 A | 12/2001 |
| JP | 2003-180804 | 7/2003 |

OTHER PUBLICATIONS

International Search Report PCT/JP2005/000196 dated Feb. 3, 2005.
European Search Report dated Mar. 12, 2008 issued in corresponding European Patent Application No. 05 70 3435.

* cited by examiner

*Primary Examiner* — Jill Warden
*Assistant Examiner* — Neil Turk
(74) *Attorney, Agent, or Firm* — Ostrolenk Faber LLP

(57) ABSTRACT

An endoscope sterilizing test pack includes an inner case having an open/close mechanism which can insert thereinto and remove therefrom an indicator for checking a sterilization effect of sterilization treatment; at least one tube connected to the inner case so that one end is opened and another end is communicated with an inside of the inner case; and a sheath member housing the tube and the inner case.

20 Claims, 26 Drawing Sheets

FIG.7
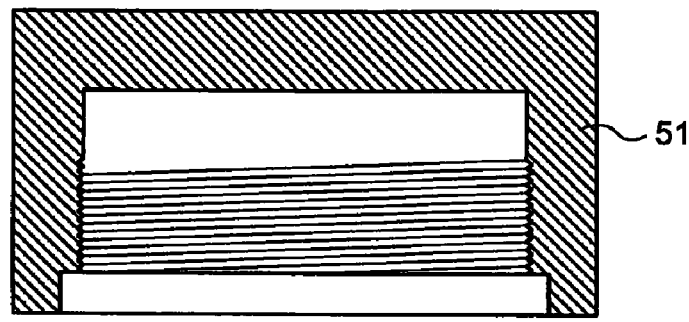
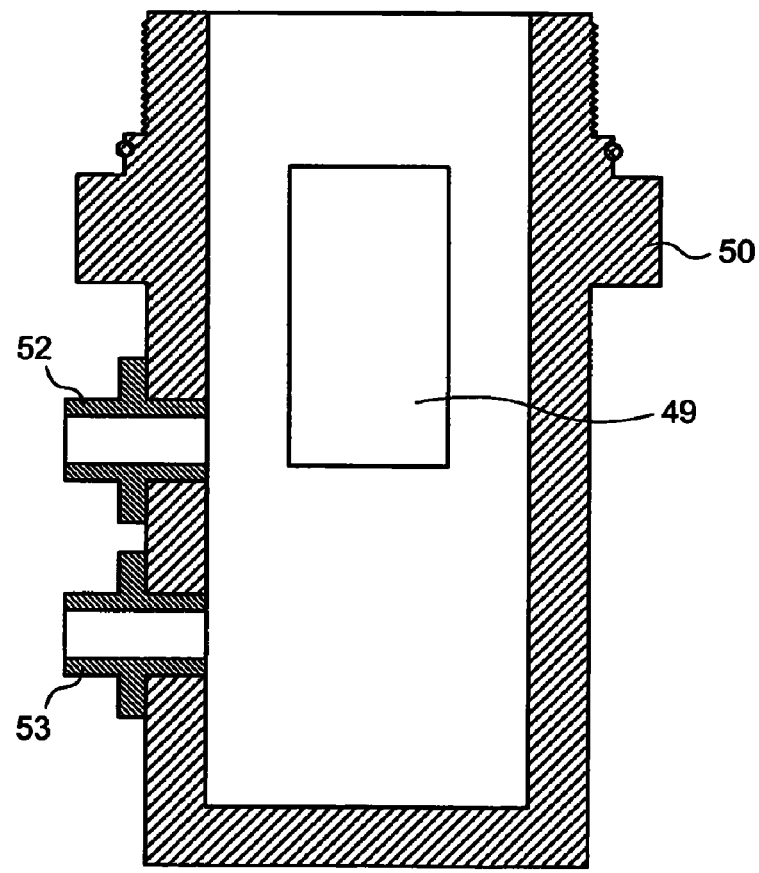

FIG.32
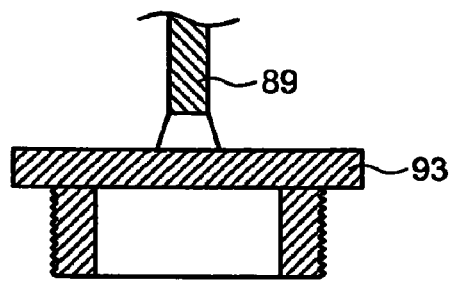
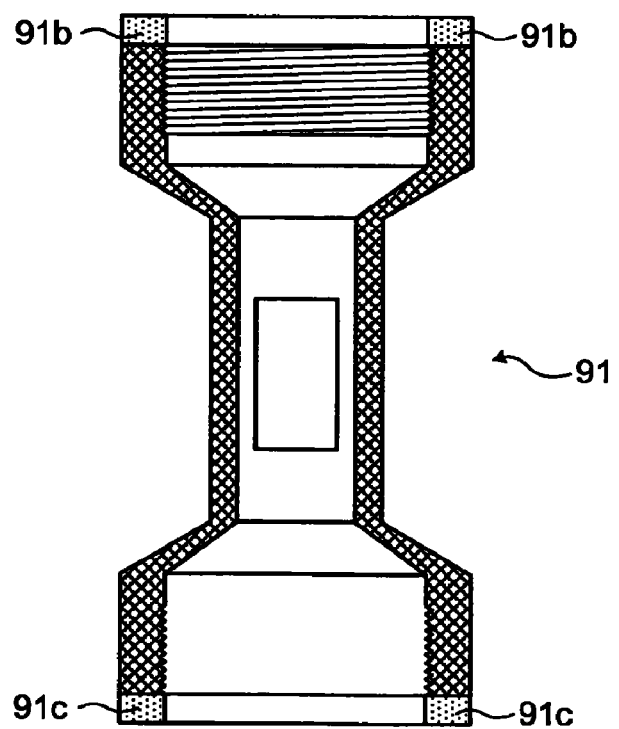
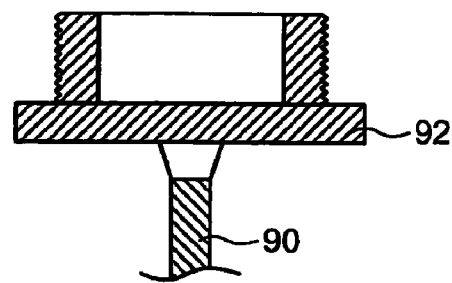

ENDOSCOPE STERILIZING TEST PACK

CROSS-REFERENCE TO RELATED APPLICATIONS

This application is a continuation of PCT international application Ser. No. PCT/JP2005/000196 filed Jan. 11, 2005 which designates the United States, incorporated herein by reference, and which claims the benefit of priority from JP-A No. 2004-003505 filed Jan. 8, 2004 and JP-A No. 2004-382118 filed Dec. 28, 2004, incorporated herein by reference.

BACKGROUND OF THE INVENTION

1. Field of the Invention

The present invention relates to a sterilizing test pack which can check a sterilization effect when a medical device required to be sterilized (or a device sterilized) is housed in a sterilizer and is subjected to sterilization treatment such as high-temperature high-pressure steam sterilization (hereinafter, called autoclave sterilization) or ethylene oxide gas sterilization (hereinafter, called EOG sterilization) by equipment sterilizing the medical device by replacing air in the chamber of the sterilizer with other gas. More specifically, the present invention relates to an endoscope sterilizing test pack corresponding to an endoscope and checking a sterilization effect.

2. Description of the Related Art

A medical device required to be sterilized (hereinafter, called a device sterilized) is typically housed in a sterilizer to be sterilized. As sterilization treatment methods, autoclave sterilization and EOG sterilization treatments have been mainstream.

Such sterilization treatment such as autoclave sterilization and EOG sterilization generally checks whether or not a sterilization effect of sterilization treatment has been sufficiently obtained.

There is a known conventional sterilization effect checking method in such a manner that when a device sterilized is sterilized by autoclave sterilization or EOG sterilization, a tape-like chemical indicator (CI) is stuck on the device sterilized or a sheet-like chemical indicator or biological indicator (BI) is inserted into an object to be sterilized.

A so-called test pack checking a sterilization effect by inserting the above-described sheet-like chemical indicator or biological indicator into the object to be sterilized has been practically used. Such test pack is constructed for autoclave sterilization and EOG sterilization or for the Bowie & Dick test conducted for checking the presence or absence of residual air in a vacuum high-pressure steam sterilizer.

Conventional techniques related with such a test pack are described, for example, in JP-A No. 5-253277 (KOKAI) and JP-A No. 2001-526399 (KOHYO).

The test pack described in JP-A No. 5-253277 (KOKAI) has a bundle of layers, porous test sheets folded to maintain integrity and positioned between the layers of the bundle and on which a steam sensitivity indicator ink is printed, plural selectable porous layers in the bundle, and at least a set of nonporous gas impermeable layers with a predetermined efficiency arranged between the porous test sheets to be separated by at least one porous layer and separated by at least one and the two porous layers.

The testing device described in JP-A No. 2001-526399 (KOHYO) has a tube made of a thermal insulating material and having a cavity defining a free space in such a manner that one end is opened for admitting a sterilizing agent and the other end is closed, and a heat absorption unit surrounding the tube, the heat absorption unit preferentially receiving heat from the cavity of the tube during use of the device in a sterilizer sodas to prevent penetration of the sterilizing agent along the cavity of the tube in the sterilization cycle by accumulated air and/or condensable gas in the free space caused by concentration on the wall of the cavity.

SUMMARY OF THE INVENTION

An endoscope sterilizing test pack according to one aspect of the present invention includes an inner case having an open/close mechanism which can insert thereinto and remove therefrom an indicator for checking a sterilization effect of sterilization treatment; at least one tube connected to the inner case so that one end is opened and another end is communicated with an inside of the inner case; and a sheath member housing the tube and the inner case.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a schematic diagram showing the construction of an inner case;

FIG. 32 is a schematic diagram showing the construction of the inner case and connection units for connecting the inner case to each of the first tube and the second tube;

DETAILED DESCRIPTION OF THE PREFERRED EMBODIMENTS

Exemplary embodiments of the present invention will be described with reference to the drawings. In the present invention, gases used for sterilizing a device such as high-temperature high-pressure steam used for autoclave sterilization and an ethylene oxide gas used for EOG sterilization are generically defined as a sterilizing gas. The following embodiments will be described by defining them in the same manner.

Figure 1:
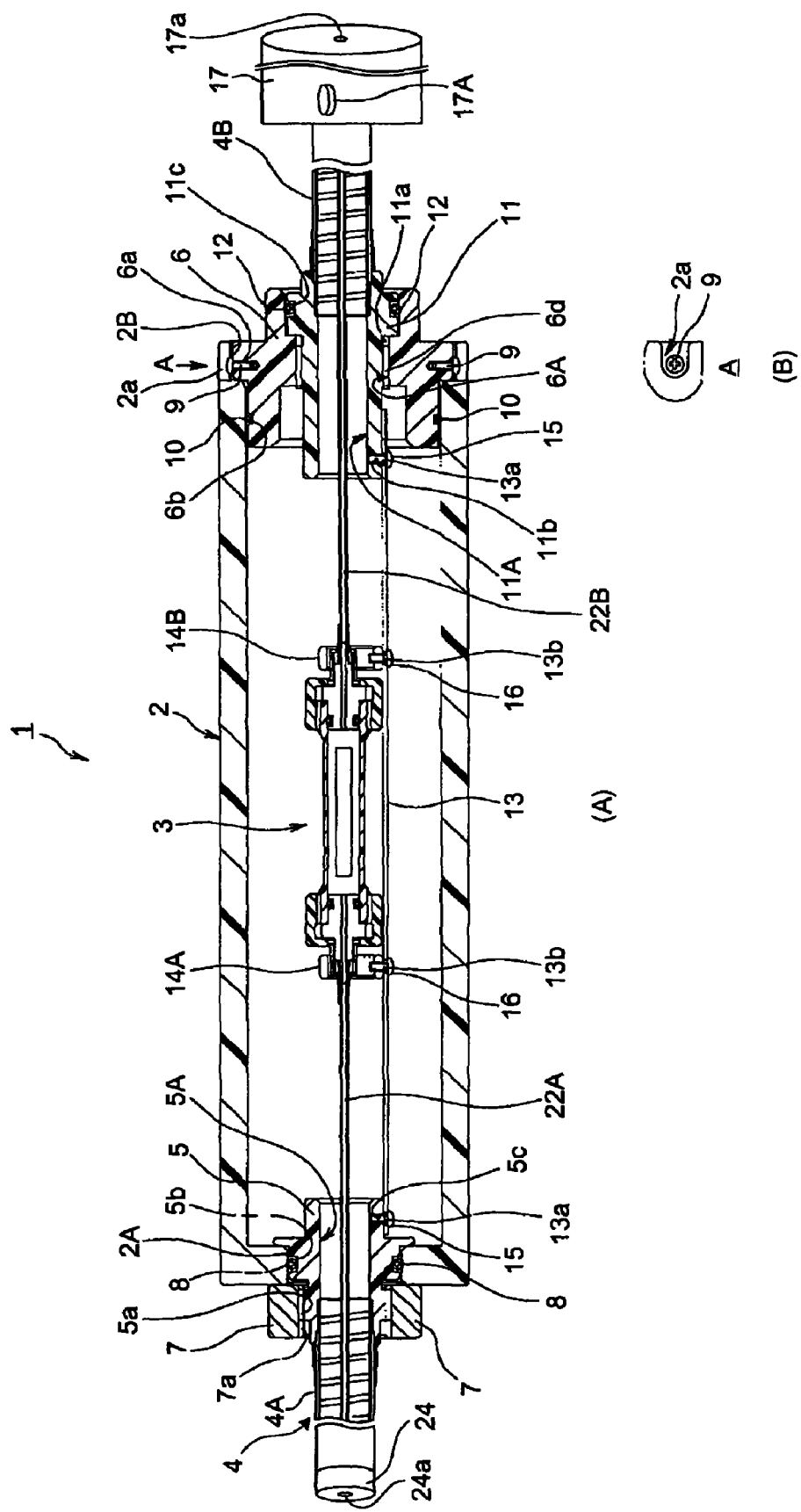
FIG. 1 is a cross-sectional view showing an embodiment of an endoscope sterilizing test pack according to the present invention and showing an entire construction of the endoscope sterilizing test pack.
Figure 2:
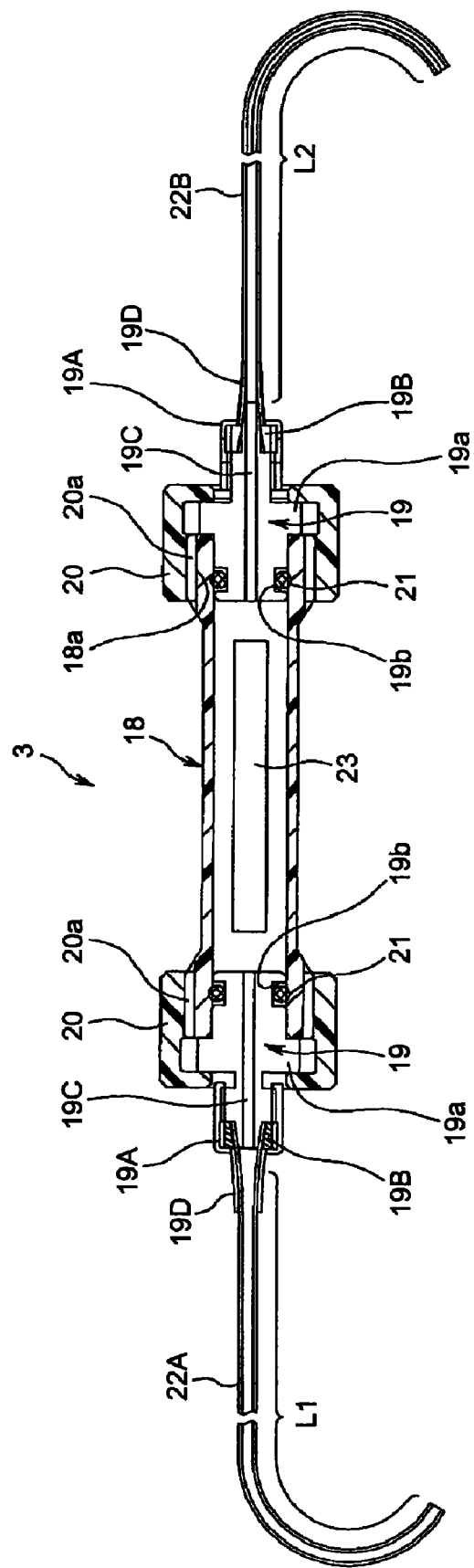
FIG. 2 is a cross-sectional view showing the construction of an inner case housed in an outer case of FIG. 1.

FIGS. 1 and 2 show an embodiment of an endoscope sterilizing test pack according to the present invention, in which (A) of FIG. 1 is a cross-sectional view showing the entire construction of the endoscope sterilizing test pack, (B) of FIG. 1 is a diagram showing a connection unit seen in the direction of arrow A in (A) of FIG. 1, and FIG. 2 is a cross-sectional view showing the construction of an inner case housed in an outer case of FIG. 1.

As shown in (A) of FIG. 1, an endoscope sterilizing test pack 1 has an outer case 2, an inner case 3 removably housed in the outer case 2, a first and a second flexible pipes 4A and 4B arranged on respective sides of the outer case 2, constructed of substantially the same shape (diameter), construction, and material as those of an insertion unit of an endoscope sterilized, not shown, and functioning as an example of a tube housing unit in the claims, two ferrules 5 and 6 fitted in respective sides of the outer case 2 and fitted with the first and second flexible pipes 4A and 4B, respectively, and a supporting member 13 holding and fixing the inner case 3 in the outer case 2.

The outer case 2 has on respective sides openings 2A and 2B. The ferrule 5 is fitted in the opening 2A by a stopping member 7. The ferrule 5 is substantially hermetically fitted in the outer case 2 in such a manner that an O-ring 8 as a sealing member is disposed in a ring groove 5b provided in part of its outer circumferential surface. The stopping member 7 has on its inner circumferential surface a screw unit 7a. The screw unit 7a engages with a screw unit 5a provided on an end side of the ferrule 5. The ferrule 5 connected to the first flexible pipe 4A is fixed and held to the outer case 2.

The ferrule 5 has in its inside a continuous hole 5A and is connected to the first flexible pipe 4A to be continued to the continuous hole 5A. A first tube 22A of the later-described inner case 3 is inserted into the first flexible pipe 4A and the ferrule 5 at an end of the outer case.

The ferrule 6 is fitted in the other opening 2B of the outer case 2. A screw 9 as a rotation stopper of the outer case 2 is fixed to the ferrule 6. The outer case 2 is provided with a notch 2a. The ferrule 6 is fitted in the state that the position of the notch 2a is matched with that of the screw 9 (see (B) of FIG. 1). The ferrule 6 is substantially hermetically fitted in the outer case 2 in such a manner that an O-ring (sealing member) 10 is disposed in a ring groove 6b provided in part of the outer circumferential surface on the inside of the outer case 2.

The ferrule 6 has in its inside a continuous hole 6A. An auxiliary ferrule 11 is mounted in the continuous hole 6A. The auxiliary ferrule 11 has on its outer circumferential surface a screw unit 11a. The auxiliary ferrule 11 is fitted in the ferrule 6 in such a manner that the screw unit 11a engages with a screw unit 6d provided on the inner circumferential surface of the continuous hole 6A. In this case, the auxiliary ferrule 11 is substantially hermetically fitted in the ferrule 6 in such a manner that an O-ring (sealing member) 12 is disposed in a ring groove 11c provided in part of the outer circumferential surface at an end side. A second tube 22B of the later-described inner case 3 is inserted into the second flexible pipe 4B and the auxiliary ferrule 11.

The supporting member 13 is formed in a plate shape and has screw holes 13a and 13a on respective ends. The supporting member 13 is fixed to the ferrule 5 and the auxiliary ferrule 11 in such a manner that screws 15 and 15 passed through the screw holes 13a and 13a are threadedly engaged with a threaded hole 5c of the ferrule 5 and a threaded hole 11b of the auxiliary ferrule 11. The supporting member 13 has near its center screw holes 13b and 13b disposed at a predetermined pitch. The supporting member 13 fixes fixing holding members 14A and 14B fixing and holding the inner case 3 in such a manner that screws 16 and 16 passed through the screw holes 13b and 13b are threaded thereon.

A rear end member 17 is substantially hermetically attached to one end of the second flexible pipe 4B. The rear end member 17 has a check valve 17A communicated with the inside of the second flexible pipe 4B. The check valve 17A can release air in the first flexible pipe 4A to the outside at a negative pressure and blocks air from the outside.

The first flexible pipe 4A has at its end a front end member 24.

In this embodiment, the endoscope sterilizing test pack provided with the rear end member 17 having the check valve 17A is described. The endoscope sterilizing test pack is not limited to this, and may omit the check valve 17A and construct a steam admission port optionally opened by a cap so as to open the ends of both the first and second flexible pipes 4A and 4B. The check valve 17A and the steam admission port are not limited to be positioned in the rear end member and may be provided in other position corresponding to the endoscope sterilized, such as in the front end member 24, the outer case 2, or the first and second flexible pipes 4A and 4B.

A specific construction of the inner case 3 will be described with reference to FIG. 2.

As shown in FIG. 2, the inner case 3 has a case body 18 formed cylindrically, ferrules 19 and 19 substantially hermetically provided in the respective ends of the case body 18 so as to close the openings on respective sides of the case body 18, fitting members 20 and 20 for removably fitting the ferrules 19 and 19 at the ends on respective sides of the case body 18 and fixing and holding them, and the first and second tubes 22A and 22B attached to the ferrules 19 and 19 and formed of substantially the same material, diameter, length, and construction as those of the duct (channel) of the endoscope sterilized (not shown).

The case body 18 has screw units 18a and 18a on the outer circumferential surfaces at the base ends on respective sides. The screw units 18a and 18a engage respectively with screw units 20a and 20a provided on the inner circumferential surfaces of the fitting members 20 and 20. The case body 18 is fitted with the fitting members 20 and 20 and the ferrules 19 and 19.

The fitting members 20 and 20 have in their insides the ferrules 19 and 19, respectively. The ferrule 19 has a flanged contact portion 19a. The ferrule 19 is fitted in the case body 18 to fasten the fitting member 20. The contact portion 19a is contacted onto the end surface of the case body 18 and is pressed by the fitting member 20 to be fixed.

The ferrules 19 and 19 are substantially hermetically fitted in the case body 18 in such a manner that O-rings (sealing members) 21 and 21 are disposed in ring grooves 19b and 19b provided in part of the outer circumferential surfaces at the ends on the case body side.

The ferrules 19 and 19 have in their insides continuous holes 19C and 19C and are connected to the first and second tubes 22A and 22B to be communicated with the continuous holes 19C and 19C. The first tube 22A is placed on the tapered edge of the ferrule 19. A cylindrical fixing unit 19B having a tapered inner circumferential surface is fastened with a nut of a connection unit 19A. The first tube 22A is fixed to the ferrule 19. A holding unit 19D is a member for preventing buckling of the first tube 22A such as a thermal shrinkage tube. The second tube 22B is also fixed to the ferrule 19 in a similar manner. The first and second tubes 22A and 22B are reliably and substantially hermetically fixed and held to the fitting members 20 and 20 by the connection units 19A and 19A.

The other end of the first tube 22A and the other end of the second tube 22B are substantially hermetically connected to the connectors provided in the front end member 24 and the rear end member 17, respectively. The rear end member 17 and the front end member 24 are formed with openings 17a and 24a as gas admission ports for leading the sterilizing gas and steam. The other end of the tube 22A and the other end of the tube 22B are adhered to the front end member 24 and the rear end member 17, respectively, by an adhesive to be communicated with the openings 24a and 17a. The adhering method may be a removable method such as connection of the first and second tubes 22A and 22B and the ferrules 19. The first and second tubes 22A and 22B, the ferrules 19, and the inner circumferential surface of the case body 18 are communicated with the outside of the endoscope sterilizing test pack 1 and are directly touched by steam and gas directly admitted from the continuous holes at sterilization.

The inner space of the first and second tubes 22A and 22B, the ferrules 19, the outer circumferential surface of the case body 18 and the outer case 2, and the first and second flexible pipes 4A and 4B is in the inside of the endoscope sterilizing test pack 1 and is substantially hermetical.

An indicator 23 is a sheet-like chemical indicator (CI) or a sheet-like biological indicator (BI) and checks a sterilization effect of sterilization treatment.

This embodiment is not limited to the above-listed indicators and may use other indicators which are housed in the case body 18 and can check a sterilization effect.

The case body 18 may be made of a transparent member which can immediately check a sterilization effect by the housed indicator 23.

In the above construction, the inner case 3 forms a duct communicated from the opening 24a of the front end member 24 via the inner surface of the first tube 22A, the continuous hole of the ferrule 19, the inside of the case body 18, the continuous hole of the ferrule 19, the inner surface of the second tube 22B, and the opening 17a of the rear end member 17. The case body 18 is disposed near the substantially center of the entire inner case 3 including the first and second tubes 22A and 22B. When autoclave sterilization or EOG sterilization is conducted, the inner case 3 is constructed so that the indicator 23 is in the farthest position from the opening of the front end member 24 or the rear end member 17 of the duct.

Various conditions such as the length, diameter, and material of the first and second tubes 22A and 22B may be suitably formed according to the endoscope sterilized. Alternatively, the first and second tubes 22A and 22B may be constructed under a condition requiring longer time for the sterilization treatment. Specifically, the first and second tubes 22A and 22B may be constructed of materials having different thermal insulation efficiency and thermal radiation efficiency so that the temperature in the case body 18 at start of the sterilization treatment is slightly lower than the temperature in the duct of the endoscope sterilized. To obtain the same sterilization effect as that of the endoscope sterilized, the sterilization treatment time may be set to be longer. The length of the tubes may be longer and the diameter of the tubes may be smaller.

Incorporated components such as other tubes, a light guide fiber, a cable, a coil, and a wire may be disposed in the endoscope sterilizing test pack 1 according to the endoscope sterilized. A volume in the first and second flexible pipes 4A and 4B and a steam flow when admitting steam into the endoscope sterilizing test pack 1 for sterilization can be closer to those of the endoscope sterilized.

In the endoscope sterilizing test pack of this embodiment, the outer case 2 is contemplated as a sheath member of the endoscope; the first and second tubes 22A and 22B, ducts inserted into the endoscope; and the space between the outer case 2 and the inner case 3, a space in the endoscope closed by the sheath member.

The operation of the endoscope sterilizing test pack of this embodiment will be described with reference to FIGS. 1 and 2.

The endoscope sterilizing test pack 1 shown in FIG. 1 is used to conduct autoclave sterilization or EOG sterilization for checking a sterilization effect. The operator turns and removes the stopping member 7 and moves the outer case 2 in the edge direction to remove it. The screw 16 is unscrewed from the supporting member 13 to remove the fixing holding member 14A.

The operator houses the indicator 23 such as a chemical indicator or a biological indicator in the inner case 3 shown in FIG. 2. In this case, the operator rotates and removes one of the fitting members 20 shown in FIG. 2, removes the ferrule 19, houses the indicator 23 of a suitable type in the case body 18, and fits the ferrule 19 and the fitting member 20 in the case body 18 again. The inside of the case body 18 is sealed by the O-rings 21. The indicator 23 housed in the inside is disposed under substantially the same setting condition as that of the duct of the endoscope sterilized or under the condition requiring longer time for sterilization treatment.

The operator straightly inserts the inner case 3 into the outer case 2 shown in FIG. 1 so as to prevent the incorporated components from getting caught by the inner case 3.

The operator fixes the outer case 2 by turning and fastening the stopping member 7.

The operator houses the endoscope sterilizing test pack 1 of FIG. 1 in a tray or a case, not shown, together with the endoscope sterilized. The tray or the case is packed in a sterilization bag or drape and is then housed in the sterilizer, not shown, to be subjected to known autoclave sterilization or EOG sterilization. In this embodiment, when vacuum high-pressure steam sterilization is conducted as sterilization treatment, it is desirable to suitably conduct the Bowie & Dick test. In such case, the indicator 23 may be replaced with an indicator suitable for the Bowie & Dick test, which may be housed in the inner case 3.

After completion of the sterilization treatment, the operator takes out the housed indicator 23 from the inner case 3 in a reverse order in which the inner case 3 is housed in the outer case 2, and then checks a sterilization effect.

In this case, the endoscope sterilizing test pack 1 is constructed so that the condition in the inner case 3 (temperature and gas concentration) is substantially the same as that in the duct of the sterilized endoscope. The indicator 23 can check the same sterilization effect as that of the actually sterilized endoscope.

In this embodiment, the presence or absence of the check valve 17A of the rear end member 17 may be determined according to the endoscope sterilized. In the case that the endoscope sterilized is of a type sterilized by admitting steam between the flexible pipes and the duct (channel), the endoscope sterilizing test pack 1 is provided just with a steam admission hole without the check valve 17A. The region of the duct in the inner case 3 (including the ducts of the first and second tubes 22A and 22B), the inside of the outer case 2, and the insides of the first and second flexible pipes 4A and 4B is communicated with the outside via the steam admission holes for conducting sterilization treatment.

In the case that the endoscope sterilized is of a type sterilized without admitting steam between the flexible pipes and the duct (channel), the endoscope sterilizing test pack 1 is provided with the check valve 17A as shown in FIG. 1. The region of the duct in the inner case 3 (including the ducts of the first and second tubes 22A and 22B), the inside of the outer case 2, and the insides of the first and second flexible pipes 4A and 4B is communicated with the outside only at a negative pressure for conducting sterilization treatment.

According to this embodiment, the endoscope sterilizing test pack having a construction corresponding to the endoscope sterilized can obtain substantially the same sterilization effect as that of the endoscope and can easily and reliably check a sterilization effect.

The present invention is not limited to the above-described embodiment and various modifications can be made within the scope without departing from the purport of the present invention.

A second embodiment of the endoscope sterilizing test pack according to the present invention will be described. The endoscope sterilizing test pack according to the second embodiment has a single tube housing unit housing two tubes. The second embodiment will be described with reference to FIGS. 3 to 10.

Figure 3:
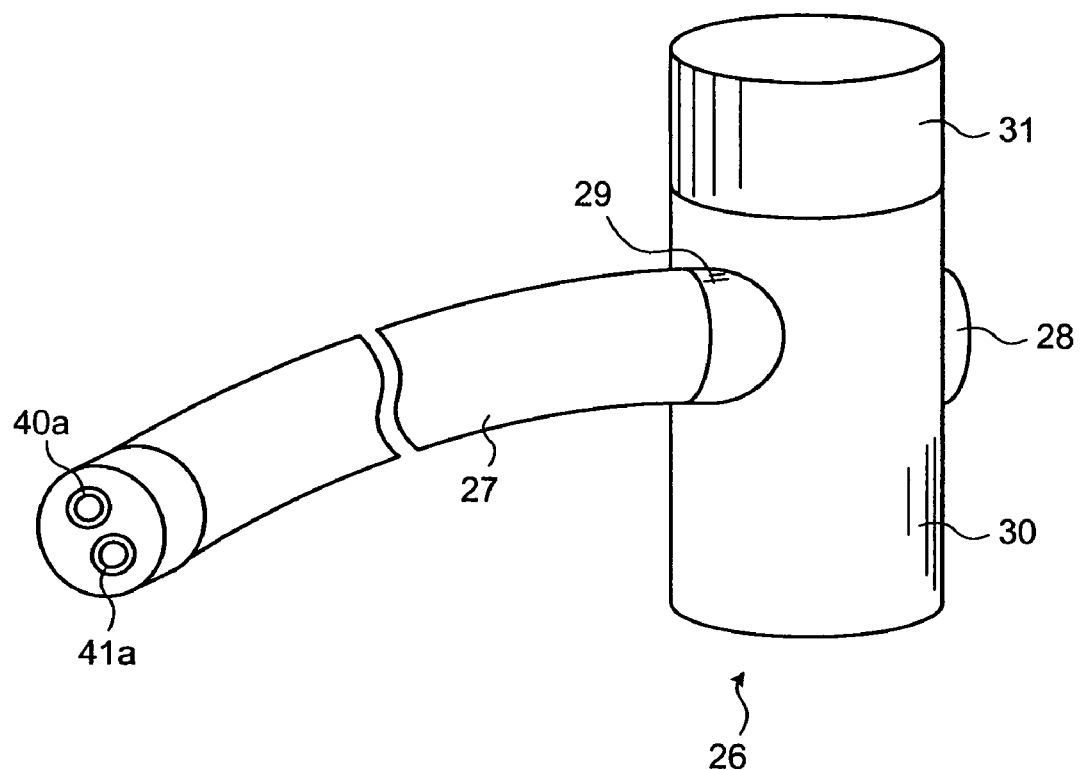
FIG. 3 is a schematic diagram showing an appearance of an endoscope sterilizing test pack according to a second embodiment.

FIG. 3 is a schematic diagram showing an appearance of the endoscope sterilizing test pack according to the second embodiment. As shown in FIG. 3, the endoscope sterilizing test pack according to the second embodiment has an outer case 26 housing an inner case 33 (not shown in FIG. 3) housing the indicator, a tube housing unit 27 housing a first tube 38 and a second tube 39 (not shown in FIG. 3), a check valve 28 for changing into substantially vacuum atmosphere the inner space of the outer case 26 and the inner space of the tube housing unit 27, that is, the periphery of the inner case 33 and the peripheries of the first and second tubes (described later) before sterilizing gas admission, and a connection unit 29 substantially hermetically coupling the tube housing unit 27 to the outer case 26.

Figure 4:
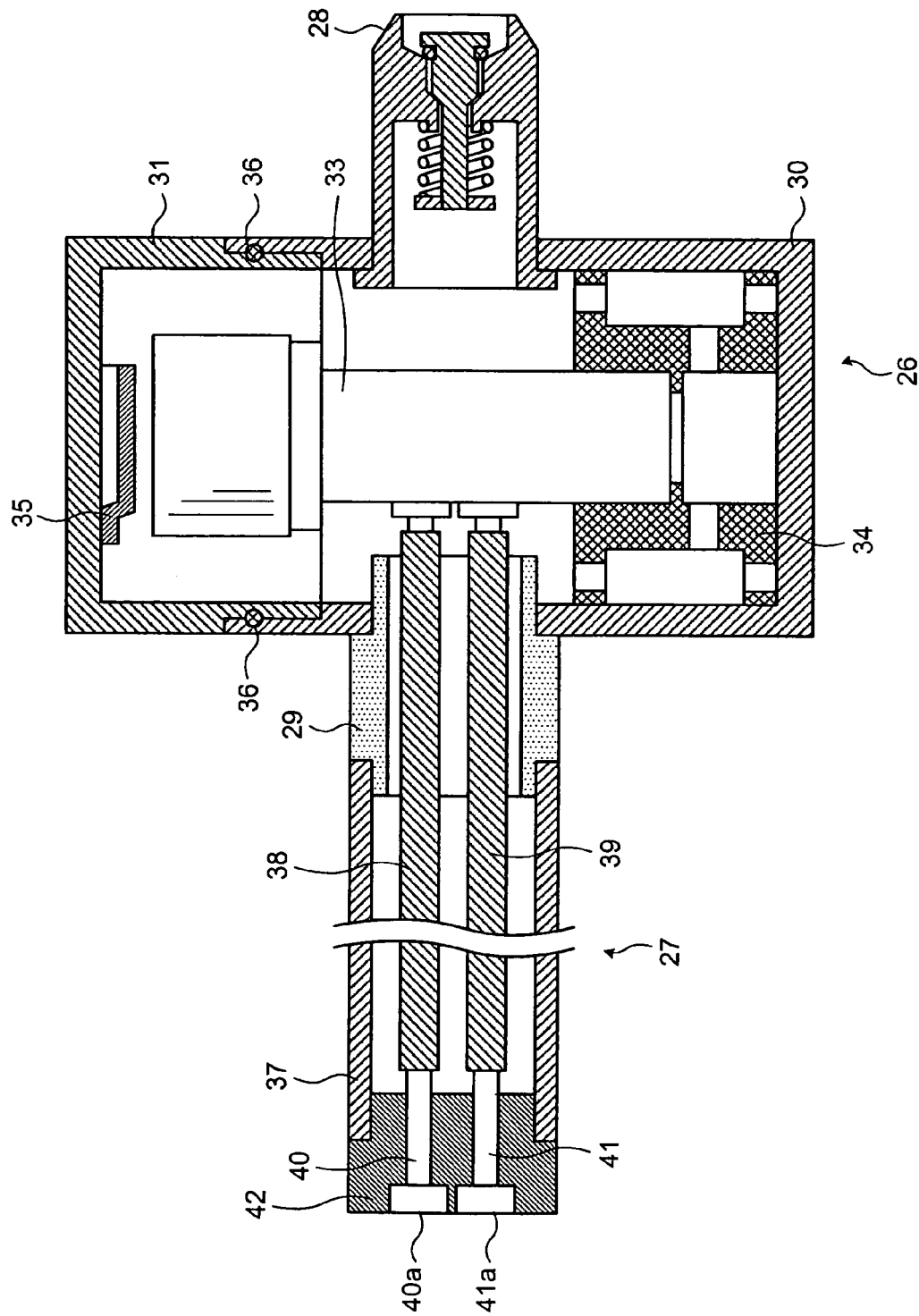
FIG. 4 is a schematic diagram showing the inner construction of the endoscope sterilizing test pack according to the second embodiment.

FIG. 4 is a schematic diagram showing the inner construction of the endoscope sterilizing test pack according to the second embodiment. As shown in FIG. 4, the endoscope sterilizing test pack according to the second embodiment has in the outer case 26 the inner case 33, a holding unit 34 holding the inner case 33, and a gas detection unit 35 detecting leakage of the sterilizing gas. The tube housing unit 27 has a flexible pipe 37 connected thereto so that the inner space of the tube housing unit 27 is communicated with the inner space of the outer case 26 via the connection unit 29 and inserting the first tube 38 and the second tube 39 thereinto, gas admission units 40 and 41 having gas admission ports 40a and 41a for admitting the sterilizing gas into the first tube 38 and the second tube 39, and an edge portion 42 connected to the distal end of the flexible pipe 37 and shielding an air gap portion (described later) in the flexible pipe 37 from the outside and holding the gas admission units 40 and 41.

The flexible pipe 37 is formed of a bendable member having flexibility, and is formed with a duct inserting both the first tube 38 and the second tube 39 thereinto. In the second embodiment, the inner diameter of the duct formed in the flexible pipe 37 is formed to be sufficiently larger than the outer diameter of the first tube 38 or the like so that an air gap is caused between the outer surfaces of the first tube 38 and the second tube 39 and the inner surface of the flexible pipe 37. Such air gap is blocked from the outer space by the function of the edge portion 42 or the like and is communicated with the inner space of the outer case 26 via the connection unit 29. When the operation of the check valve 28 changes the inner space of the outer case 26 into substantially vacuum atmosphere, the air gap portion in the flexible pipe 37 is also changed into substantially vacuum atmosphere.

As in the first embodiment, the flexible pipe 37 may be constructed of the same shape (diameter), construction, and material as those of the insertion unit of the endoscope. There may be used other tubular members in which temperature rise of the inner walls of the first tube 38 and the second tube 39 is the same as that of the case using the insertion unit of the endoscope or temperature rise is more difficult.

As in the first tube 22A and the second tube 22B of the first embodiment, the first tube 38 and the second tube 39 admit the sterilizing gas into the indicator provided in the inner case 3. The endoscope sterilizing test pack according to the second embodiment checks whether or not the endoscope has been reliably sterilized. The first tube 38 and the second tube 39 of the second embodiment have a construction corresponding to the duct provided in the endoscope sterilized and are formed so that a condition of the sterilizing gas reaching a region in which the indicator is disposed (that is, the inner region of the inner case 33) is equal to or more strict than that of the midpoint of the duct formed in the endoscope sterilized. The outer circumferences of the first tube 38 and the second tube 39 may be contacted or may not be contacted with the inner circumference of the flexible pipe 37 unless temperature rise of the tubes and the passing of the sterilizing gas in the tubes is affected, i.e., as far as the sterilization effect is not affected.

The outer case 26 houses the inner case 33 incorporating the indicator and maintains the periphery of the inner case 33 in a predetermined atmosphere or substantially vacuum atmosphere in the second embodiment at sterilizing gas admission. Specifically, the outer case 26 has a housing case 30 housing the inner case 33, and a cap top 31 thread jointed, for example, to the housing case 30 and formed to be removable therefrom. An O-ring 36 is arranged in the portion of the housing case 30 contacted with the cap top 31 when they are fitted. The cap top 31 is substantially hermetically fitted to the housing case 30 by the operation of the O-ring 36.

The gas detection unit 35 arranged in the outer case 26 determines whether or not the sterilizing gas admitted into the inner case 33 through the first tube 38 and the second tube 39 has been leaked to the outside of the inner case 33 or determines whether or not the hermeticity of the members has been deteriorated and the sterilizing gas has entered from the outside through an unintended portion into the test pack. Specifically, the gas detection unit 35 is formed of an indicator such as an index or CI coated with a chemical reacted with the target sterilizing gas and a mechanism housing the indicator and has the function of detecting leakage and unintended entry of the sterilizing gas in such a manner that the indicator indicates a predetermined reaction when the sterilizing gas is leaked to the outside of the inner case 33.

The presence or absence of leakage and unintended entry of the sterilizing gas is preferably detected for each sterilization treatment. The gas detection unit 35 is preferably arranged in the position easily withdrawing the indicator for each completion of sterilization treatment. In the second embodiment, the gas detection unit 35 is arranged on the inner surface of the cap top 31 constructing the outer case 26. The gas detection unit 35 arranged in such position can withdraw the indicator when the cap top 31 is removed from the housing case 30 more easily than the gas detection unit 35 arranged in the bottom portion of the housing case 30.

The check valve 28 arranged on the outer case 26 will be described. As in the first embodiment, the check valve 28 changes the inner space of the outer case 26 into substantially vacuum atmosphere and maintains the substantially vacuum atmosphere. The endoscope sterilization treatment is generally conducted by admitting the sterilizing gas into the chamber after a predetermined space region (that is, the inside of the chamber) in the sterilizer into which the endoscope (and the endoscope sterilizing test pack) is introduced is vacuum drawn. The check valve 28 has the function of passing the gas from the inside of the outer case 26 only in the direction toward the outer space. The check valve 28 has the function of forming substantially vacuum atmosphere by releasing the gas in the outer case 26 to the outer space in the vacuum drawing process performed in the sterilization treatment to maintain the inner space of the outer case 26 and the inner space of the tube housing unit 27 in substantially vacuum atmosphere in such a manner that the check valve 28 is closed when the sterilizing gas is admitted into the chamber after the vacuum drawing.

Figure 5:
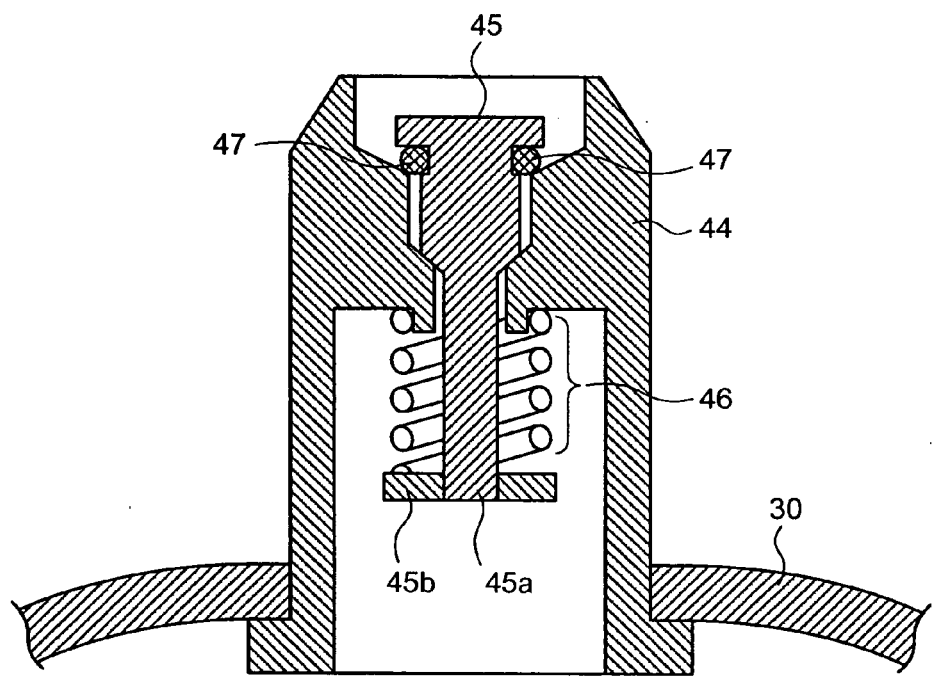
FIG. 5 is a schematic diagram showing the construction of a check valve.

FIG. 5 is a schematic diagram showing the construction of the check valve 28. As shown in FIG. 5, the check valve 28 has a body case 44 formed with a throughhole communicating the outer space with the inner space of the outer case 26 (the housing case 30), a piston 45 arranged to be slid in the throughhole formed in the body case 44 and having a piston body 45a, a spring member 46 exerting a resilience force to the piston 45 in the direction approaching the outer case 26 (the housing case 30) (in the lower direction in FIG. 5), a spring stop member 45b as part of the piston 45 for arranging the spring member, and an O-ring 47 for substantially hermetically maintaining the piston 45 and the body case 44 when the valve is closed.

The piston body 45a has a large diameter portion formed with a groove arranging the O-ring 47, and a small diameter portion having an outer diameter smaller than the large diameter portion and capable of screwing the spring stop member 45b to its edge. The spring member 46 is arranged in the periphery of the small diameter portion. The spring stop member 45b is formed with a screw hole in its center and is screwed to the edge of the piston body 45a using such screw hole. The spring force amount of the spring member 46 arranged in the periphery of the small diameter portion of the piston body 45a is set to a force amount in which the check valve 28 is operated at a given pressure. The throughhole formed in the body case 44 is formed to include a first space corresponding to the position of the large diameter portion of the piston body 45a and a second space as a portion in which the spring member 46 is arranged and is formed to have an inner diameter so that the small diameter portion of the piston body 45a can be inserted between the first and second spaces and that the large diameter portion cannot be inserted therebetween. The spring member 46 is arranged to be interposed between the spring stop member 45b and the body case 44 in the second space. When the pressure of the outer space has a value equal to or higher than that of the pressure of the inner space of the outer case 26, the piston 45 is exerted to the outer case 26 side by the spring member 46. As shown in FIG. 5, the sloped surface of the first space formed in the body case 44 is contacted with the O-ring 37 to block the communicated state of the outer space and the inner space of the outer case 26. Typically, the check valve 28 is in the blocked state (the valve is closed).

Figure 6:
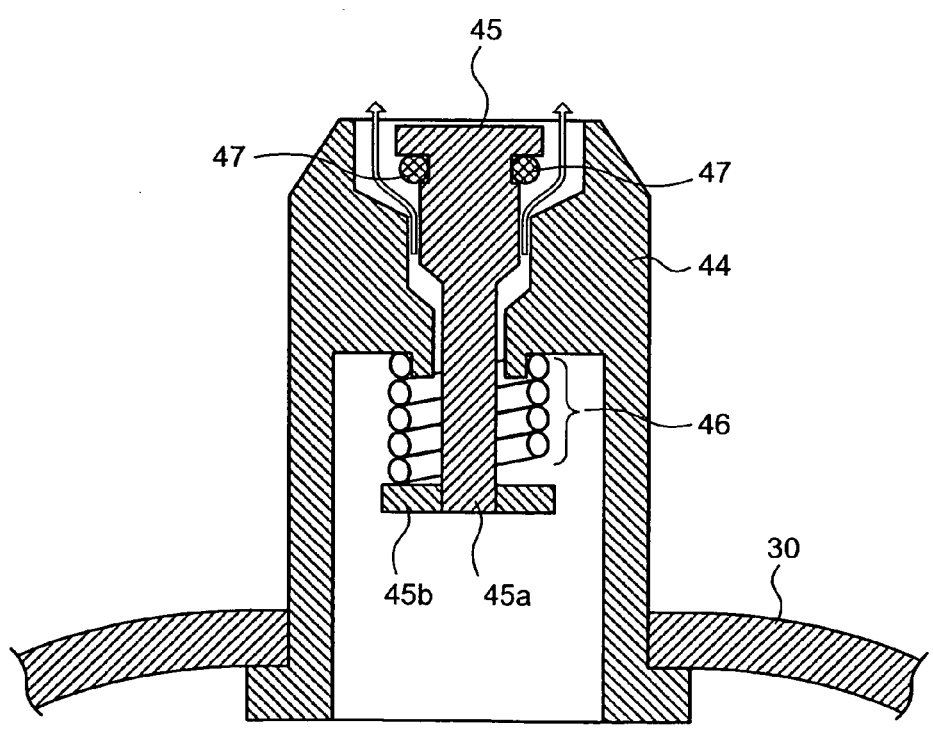
FIG. 6 is a schematic diagram showing the construction of the opened check valve.

In the vacuum drawing process prior to sterilizing gas admission, the piston is moved to the outer space side to release the contacted state of the sloped portion of the first space and the O-ring 47 (the valve is opened). FIG. 6 is a schematic diagram showing such state. In the vacuum drawing process, the gas is discharged to the outside by the operation of a predetermined vacuum pump or the like and the pressure in the outer space is lower than that in the inner space of the outer case 26. As an outer force acting on the piston 45, the pressure of the gas present in the inner space of the outer case 26 is predominant. The piston 45 is moved in the outer space direction (the upper direction in FIG. 6) to release the contacted state of the sloped portion of the first space formed in the body case 44 and the O-ring 47. The outer space is communicated with the inner space of the outer case 26 through the air gap portion between the throughhole and the piston 45. The outer space is vacuum drawn. The gas in the outer case 26 passes through the air gap portion to be discharged to the outer space. The inner space of the outer case 26 is changed into substantially vacuum atmosphere.

As described above, in the sterilization treatment by the sterilizer, the sterilizing gas is admitted after completion of the vacuum drawing. In such process, the pressure in the outer space has a value larger than that of the pressure (substantially vacuum atmosphere) in the inner space of the outer case 26. The piston 45 is maintained in the state that the sloped portion of the first space formed in the body case 44 is contacted with the O-ring 47 (that is, the state shown in FIG. 5). The outer space is not communicated with the inner space of the outer case 26. The substantially vacuum atmosphere formed in the inner space of the outer case 26 is maintained during the sterilizing gas admission process.

The inner case 33 housed in the outer case 26 will be described. As in the inner case 3 of the first embodiment, the inner case 33 holds in its inside the indicator for determining whether or not the endoscope sterilized has been suitably sterilized and admits the sterilizing gas to such indicator through the first tube 38 and the second tube 39.

FIG. 7 is a schematic diagram showing the construction of the inner case 33. As shown in FIG. 7, the inner case 33 has a case body 50 housing an indicator 49, a cap 51 formed to be removable from the case body 50, an O-ring substantially hermetically sealing the case body 50 and the cap 51, and connection units 52 and 53 for communicating the inside of the case body 50 with the first tube 38 and the second tube 39, respectively. The connection units 52 and 53 are substantially hermetically fixed to the case body 50.

The cap 51 is formed to be removable from an opening formed in the case body 50. Specifically, a screw groove is formed in the portion of the cap 51 connected to the inner case body 50 and the cap 51 is thread jointed to a thread formed in the corresponding portion of the case body 50 so that the cap 51 is fitted to the case body 50. The cap 51 has a surface contacted with the O-ring provided in the case body 50, as described later.

Figure 8:
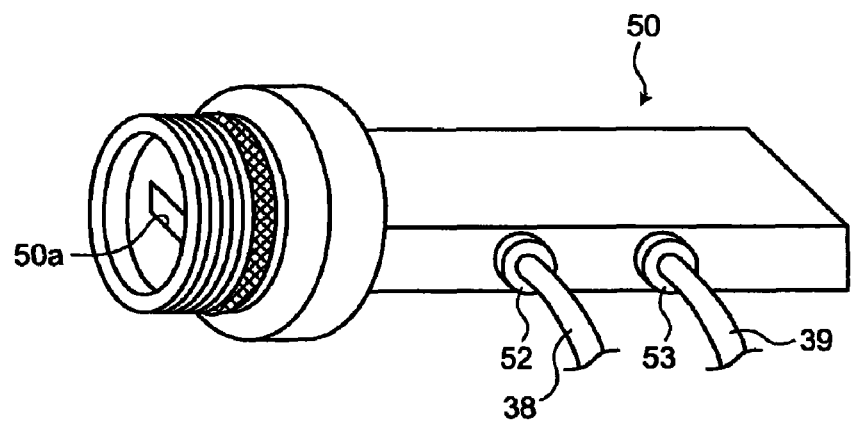
FIG. 8 is a schematic diagram showing an appearance of a case body.

The case body 50 will be described. FIG. 8 is a schematic diagram showing an appearance of the case body 50. As shown in FIG. 8, the case body 50 has, in addition to the portion formed with the thread for fitting the cap 51 therewith, an O-ring for substantially hermetically sealing the same, and a holding portion of the indicator 49 formed in a plate shape. A slit 50a is formed near the portion formed with the thread. The indicator 49 is inserted into and removed from the space in the case body 50 through the slit 50a.

The holding unit 34 will be described. The holding unit 34 stably holds the inner case 33 in the outer case 26. As shown in FIG. 4, the holding unit 34 is fixed to the inner surface of the housing case 30 constructing the outer case 26 and has the function of holding the inner case 33.

Figure 9:
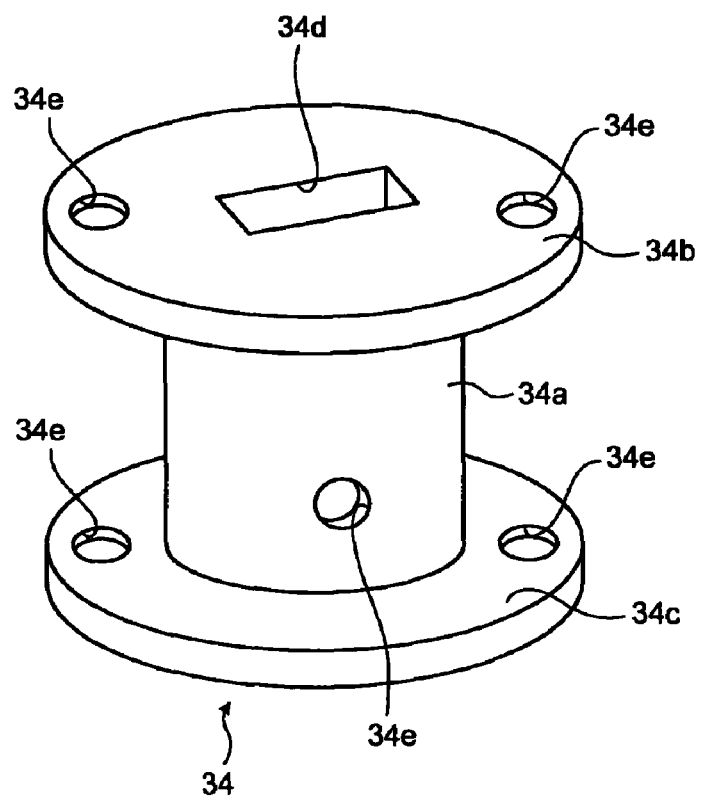
FIG. 9 is a schematic diagram showing the construction of a holding unit.

FIG. 9 is a schematic diagram showing the construction of the holding unit 34. As shown in FIG. 9, the holding unit 34 has a construction in which fins 34b and 34c are formed integrally with the upper and lower sides of a holing unit body 34a formed cylindrically. The fin 34b is formed with a case insertion unit 34d for inserting the inner case 33 thereinto. The holding unit body 34a and the fins 34b and 34c are suitably formed with vents 34e. As shown in the cross-sectional view of the holding unit 34 of FIG. 4, the inner surface of the case insertion unit 34d is formed with a protrusion portion for positioning.

The fins 34b and 34c are formed to have a value of the outer diameter substantially equal to that of the inner diameter of the housing case 30. In such construction, the holding unit 34 is arranged in the housing case 30 with no clearance. The holding unit 34 is adhered and fixed to the housing case 30.

The case insertion unit 34d is formed in a slit corresponding to the plate-like portion of the case body 50 constructing the inner case 33. The plate-like portion is inserted into the case insertion unit 34d to be adhered and fixed. The inner case 33 is held by the holding unit 34. Such a manner of holding is advantageous for insertion and removal of the indicator 49. As described above, the cap 51 constructing the inner case 33 is thread jointed to the case body 50 to be inserted thereinto and removed therefrom. The cap 51 inserted and removed exerts a circumferential force to the case body 50. The case body 50 is inserted into the case insertion unit 34d formed in a slit to be fixed. Co-rotation such that the case body 50 is rotated by such circumferential force can be prevented. In particular, in the second embodiment, the body case is connected to the first tube 38 and the second tube 39 via the connection units 52 and 53. Co-rotation is prevented to avoid any damage of the first tube 38 or the like.

The vents 34e prevent a closed space from being formed in the housing case 30 when the holding unit 34 is arranged in the housing case 30. For instance, the holding unit body 34a constructing the holding unit 34 is formed cylindrically so that an air gap portion exists inside. When such air gap portion forms the closed space and a gas discharge operation is performed by the check valve 28, air in the closed space cannot be discharged. The pressure state in the test pack cannot be uniform. The vents 34e are formed in the respective positions to maintain a satisfactory communicated state with other space regions.

The height of the holding unit 34 and the amount of the inner case 33 inserted into the case insertion unit 34d can be optionally set. In the second embodiment, as a preferred example, the height of the holding unit 34 and the amount of the inner case 33 inserted into the case insertion unit 34d can be previously set so that the upper end of the cap 51 as the component of the inner case 33 held in the holding unit 34 is above the opening portion of the housing case 30. A protrusion portion for positioning is provided on the inner surface of the case insertion unit 34d so that assembling is easy.

Figure 10:
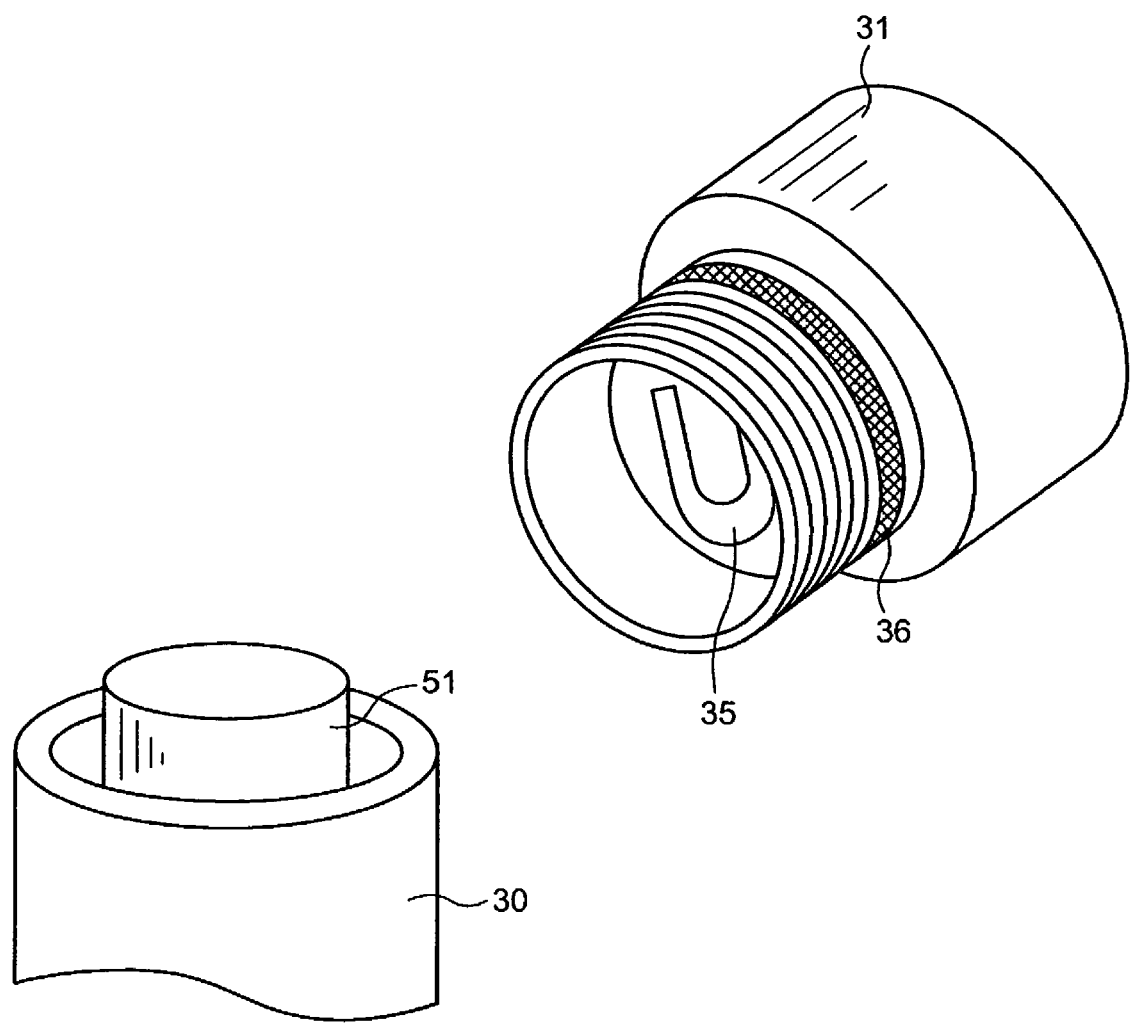
FIG. 10 is a schematic diagram showing the state that a cap top constructing an outer case is removed from a housing case.

FIG. 10 is a schematic diagram showing the state that the cap top 31 constructing the outer case 26 is removed from the housing case 30. As shown in FIG. 10, in the second embodiment, when the cap top 31 is removed, the construction of the holding unit 34 and the inner case 33 is set so that the upper end of the cap 51 as the component of the inner case 33 housed in the housing case 30 is protruded upward from the opening portion of the housing case 30. In such construction, after completion of the sterilization treatment, the user can easily hold and remove the cap 51 when the indicator 49 housed in the inner case 33 is removed. The construction of the second embodiment is described above. The respective units are assembled to maintain a substantially hermetic state. Only the cap top 31 of the outer case 26 and the cap 51 of the inner case 33 can be inserted into and removed from the housing case 30 and the case body 50.

A method of using the endoscope sterilizing test pack according to the second embodiment will be briefly described. The endoscope sterilizing test pack according to the second embodiment needs to set in its inside the chemical or biological indicator 49 checking a sterilization effect of the target sterilizer. The cap top 31 is unscrewed from the housing case 30 and the cap 51 of the inner case 33 is then unscrewed. The slit 50a of the inner case appears. The indicator 49 is inserted into the slit 50a. After the indicator 49 is inserted into the inner case 33, the cap 51 is attached to the case body 50 and the cap top 31 is attached to the housing case 30. The respective cases and caps are screwed to each other so that they can be maintained in a substantially hermetical state and that the respective caps cannot be removed due to pressure change in the sterilized device. The endoscope sterilizing test pack is carried into a predetermined sterilizer together with the endoscope sterilized and is sterilized under the same condition as that of the endoscope. In the vacuum drawing process performed as a pre-process of the sterilizing gas admission, the operation of the check valve 28 changes the inner space of the outer case 26 and the inner space of the tube housing unit 27, more specifically, the periphery of the inner case 33 and the peripheries of the first tube 38 and the second tube 39 into substantially vacuum atmosphere. The check valve 28 can communicate the inner space of the outer case 26 with the outside under the pressure condition and communicate the inner space of the tube housing unit 27 with the inner space of the outer case 26 through the inner space of the connection unit 29. As described above, the inside of the endoscope sterilizing test pack is brought into a uniform substantially vacuum state.

Thereafter, the sterilizing gas is admitted. The sterilizing gas flows through the gas admission ports 40a and 41a into the first tube 38 and the second tube 39 to reach the inside of the inner case 33. The indicator 49 is held in the inner case 33. The reached sterilizing gas acts on the indicator 49. In such process, the check valve 28 blocks the outer space and the inner space of the outer case 26. The inner space of the outer case 26 and the inner space of the tube housing unit 27 are maintained in substantially vacuum atmosphere without admitting the sterilizing gas.

The endoscope sterilizing test pack according to the second embodiment is taken out from the sterilizer together with the endoscope sterilized to check a sterilization effect. The cap top 31 constructing the outer case 26 and the cap 51 constructing the inner case 33 are removed to take out the indicator 49 housed in the inner case 33. The sterilized state of the indicator 49 is checked to determine whether or not the endoscope sterilized has been sufficiently sterilized. As in the checking of the indicator 49, the presence or absence of leakage and unintended entry of the sterilizing gas is checked in the gas detection unit 35. Whether or not the periphery of the inner case 33 is maintained in substantially vacuum atmosphere at sterilizing gas admission is checked.

An advantage of the second embodiment will be described. As in the first embodiment, the endoscope sterilizing test pack according to the second embodiment is sterilized in the sterilizer together with the endoscope sterilized to determine whether or not the endoscope has been sufficiently sterilized without directly inspecting the inside of the endoscope. The endoscope sterilizing test pack according to the second embodiment admits the sterilizing gas into the inner case 33 through the first tube 38 and the second tube 39 having the same construction as that of the duct formed in the endoscope sterilized. The reaching condition of the sterilizing gas to the inner case 33 is almost the same as that of the midpoint of the duct provided in the endoscope. The sterilizing gas reaches the indicator 49 arranged in the inner case 33 under almost the same condition as that of the midpoint of the duct of the endoscope. The reacted state of the indicator 49 is checked to correctly determine the sterilized state of the endoscope (more specifically, the midpoint of the duct of the endoscope as a portion in which sterilization is most difficult).

In the second embodiment, as in the first embodiment, the operation of the check valve 28 maintains the periphery of the inner case 33 in substantially vacuum atmosphere at sterilizing gas admission. The temperature of the indicator 49 housed in the inner case 33 is changed only by the sterilizing gas admitted through the first tube 38 and the second tube 39. More correctly, a sterilization environment equal to or more strict than that of the duct formed in the endoscope can be realized.

General sterilization treatment is conducted by exposing the endoscope to sterilizing gas atmosphere under a predetermined high-temperature condition. To sufficiently conduct the sterilization treatment, the object to be sterilized needs to be heated to a predetermined temperature. When the heat transmission efficiency from the outer space to the inner case 33 is higher than that from the outer space to the midpoint of the duct of the endoscope sterilized, the indicator 49 arranged in the inner case 33 is placed in a sterilization environment gentler than that of the midpoint of the duct. The determination accuracy of the sterilized state of the endoscope can be lowered. In particular, the inner case 33 need to employ a construction having a surface area larger than that of the duct of the endoscope to house the indicator 49. When a heat transmission substance such as a gas remains in the periphery of the inner case 33, the possibility that the heat transmission efficiency can be higher than that of the duct of the endoscope is high.

As in the first embodiment, the second embodiment employs a construction in which the periphery of the inner case 33 is maintained in substantially vacuum atmosphere at sterilizing gas admission. As known, the substantially vacuum atmosphere indicates very excellent thermal insulation properties. Heat transmission directly performed from the outer space to the inner case 33 (that is, not depending on the sterilizing gas passed through the first tube 38 and the second tube 39) can be substantially neglected. The endoscope sterilizing test pack according to the second embodiment can realize a sterilization environment substantially equal to or more strict than that of the duct provided in the endoscope in view of the heat transmission efficiency.

The endoscope sterilizing test pack according to the second embodiment houses plural tubes in the single tube housing unit 27. As shown in FIG. 3, the endoscope sterilizing test pack according to the second embodiment can realize a simple appearance construction and can be easily handled by the user.

The second embodiment employs a construction in which the peripheries of the first tube 38 and the second tube 39 are maintained in substantially vacuum atmosphere at sterilizing gas admission corresponding to the first tube 38 and the second tube 39 housed in the single tube housing unit 27. The tubes close to each other can be affected each other in terms of heat transmission.

In the second embodiment, the peripheries of both the first tube 38 and the second tube 39 are maintained in substantially vacuum atmosphere at sterilizing gas admission. Heat transmission can be prevented between the first tube 38 and the second tube 39 and heat transmission of the respective ducts is not affected. By employing such construction, the sterilization environment in the endoscope sterilizing test pack can be more strict than that of the endoscope. A sterilized state can be determined more reliably.

The endoscope sterilizing test pack according to the second embodiment has the gas detection unit 35 detecting flow of the sterilizing gas into the inner space of the outer case 26. As apparent from the above description, the inside of the outer case 26 in which the inner case 33 is arranged needs to be maintained in substantially vacuum atmosphere at sterilizing gas admission. When the hermeticity of the outer case 26 is insufficient, the operation of the check valve 28 changes the inside of the outer case 26 into substantially vacuum atmosphere in the vacuum drawing process, the sterilizing gas is flowed into the inner space of the outer case 26 at sterilizing gas admission to destroy the substantially vacuum atmosphere. When the substantially vacuum atmosphere is destroyed, the above-described thermal insulation effect cannot be expected. The reliability of the sterilized state determination of the endoscope by the endoscope sterilizing test pack is lowered. In the second embodiment, the gas detection unit 35 is arranged to check the presence or absence of such inflow of sterilizing gas. When the gas detection unit 35 detects flow of the sterilizing gas into the inner space of the outer case 26, another test pack is used to sterilize the endoscope again. Even if a problem arises in the construction of the outer case 26, for example, due to deterioration with time, the malfunction can be detected immediately in the second embodiment.

Modification Example 1 of the second embodiment will be described. An endoscope sterilizing test pack according to Modification Example 1 has a mechanism detecting whether or not the inner space of the outer case 26 and the tube housing unit 27 (in other words, the peripheries of the inner case 33, the first tube 38, and the second tube 39) are maintained in substantially vacuum atmosphere at sterilizing gas admission.

Figure 11:
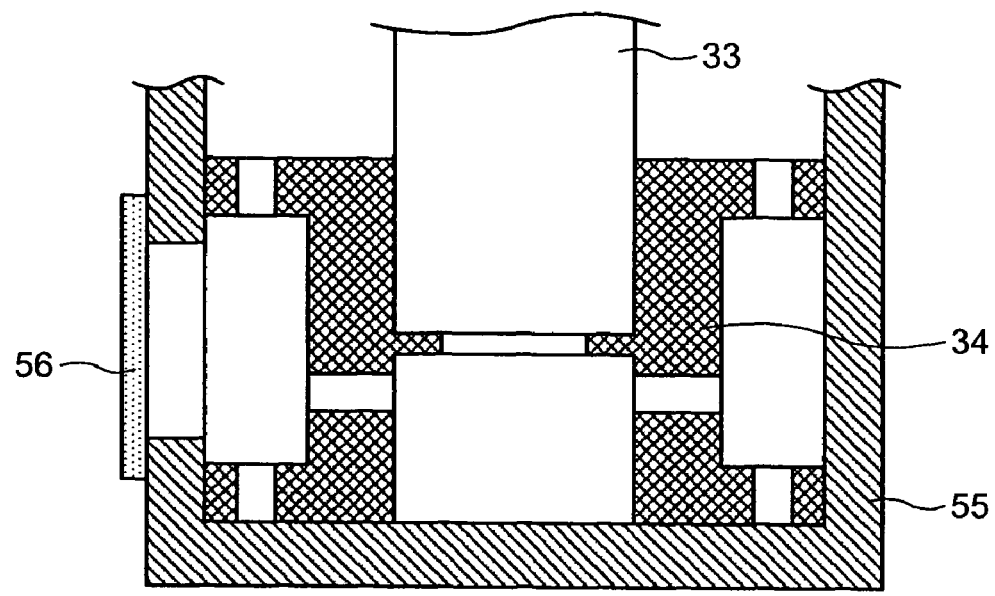
FIG. 11 is a schematic diagram showing the construction of an endoscope sterilizing test pack according to Modification Example 1 of the second embodiment.

FIG. 11 is a schematic diagram showing such mechanism and the construction therearound. As shown in FIG. 11, a housing case 55 as the component of the outer case is formed with a throughhole communicated with the outer space in addition to the portion connected to the cap top 31. In the endoscope sterilizing test pack according to Modification Example 1, a soft sheet 56 is substantially hermetically adhered and fixed to cover such throughhole.

The soft sheet 56 functions as a vacuum detection unit detecting whether or not the inside of the housing case 55 is maintained in substantially vacuum atmosphere. Specifically, the soft sheet 56 is formed of a flexible sheet-like member having hermeticity, and has a characteristic blocking movement of the gas between the outer space and the inner space of the housing case 55 and being easily deformed according to the magnitude relation between the pressure of the outer space and the pressure of the inner space of the housing case 55. The soft sheet 56 uses such characteristic to detect whether or not the inner space of the housing case 55 is maintained in substantially vacuum atmosphere.

Figure 12:
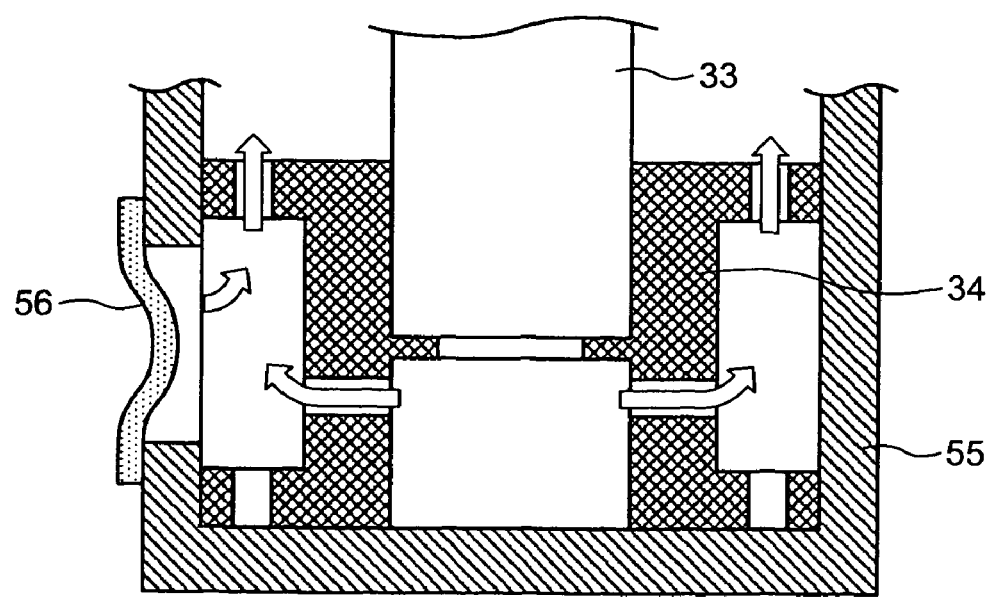
FIG. 12 is a schematic diagram of assistance in explaining the operation of a soft sheet.

FIG. 12 is a schematic diagram showing the state that the endoscope sterilizing test pack according to Modification Example 1 is taken out from the sterilizer at completion of the sterilization treatment. When the respective components of the endoscope sterilizing test pack function properly, the operation of the check valve 28 maintains the inner space of the housing case 55 in substantially vacuum atmosphere. Such substantially vacuum atmosphere is maintained unless the cap top 31 constructing the outer case together with the housing case 55 is removed. When the endoscope sterilizing test pack is taken out from the sterilizer to be placed under an atmospheric pressure condition, the pressure in the outer space has a value higher than that in the inner space of the housing case 55. The soft sheet 56 is deformed in a concave shape, seen from the outer space, according to such difference in pressure. The user checks the shape of the soft sheet 56 to easily determine whether or not substantially vacuum atmosphere is maintained. Whether or not the endoscope sterilizing test pack has been suitably sterilized can be easily determined.

Figure 13:
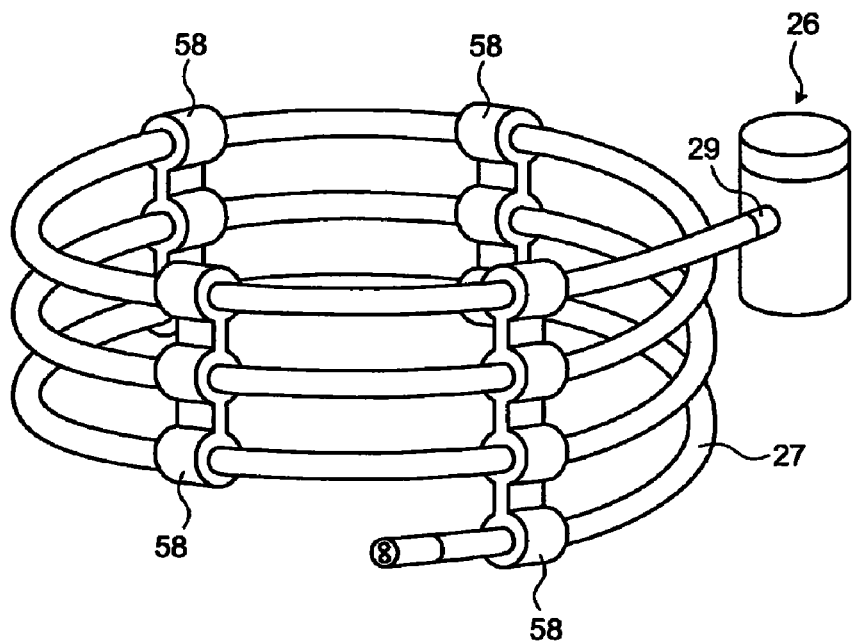
FIG. 13 is a schematic diagram showing an appearance of an endoscope sterilizing test pack according to Modification Example 2 of the second embodiment.

Modification Example 2 of the second embodiment will be described. The endoscope sterilizing test pack according to Modification Example 2 has holders spirally holding the tube housing unit 27. FIG. 13 is a schematic diagram showing an appearance of the endoscope sterilizing test pack according to Modification Example 2. As shown in FIG. 13, Modification Example 2 has holders 58 spirally holding the tube housing unit 27.

Figure 14:
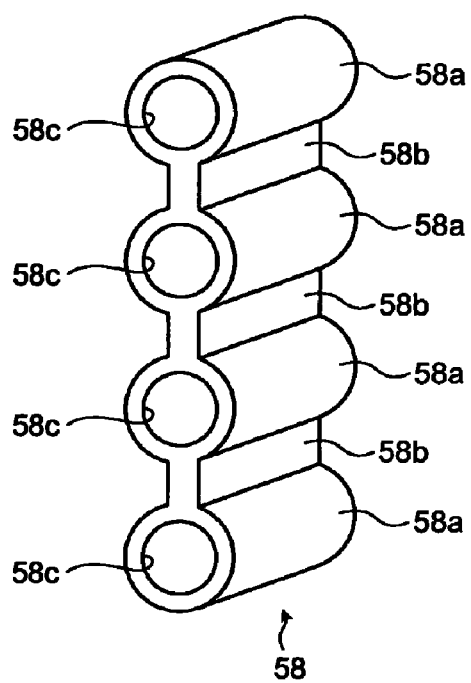
FIG. 14 is a schematic diagram showing the construction of a holder.

FIG. 14 is a schematic diagram showing the construction of the holder 58. As shown in FIG. 14, the holder 58 has a construction in which plural insertion units 58a formed with ducts 58c for inserting the tube housing unit 27 thereinto are formed integrally with connection units 58b connecting the adjacent insertion units 58a. The thus-constructed holder 58 holds the tube housing unit 27 inserted into the ducts 58c. As shown in FIG. 13, the tube housing unit 27 can be spirally held. The tube housing unit 27 is held in the state shown in FIG. 13. The occupied area of the endoscope sterilizing test pack can be smaller in the sterilizer. The endoscope sterilizing test pack according to Modification Example 2 facilitates handling as compared with the endoscope sterilizing test pack in which the tube housing unit 27 is uniformly extended.

Figure 15:
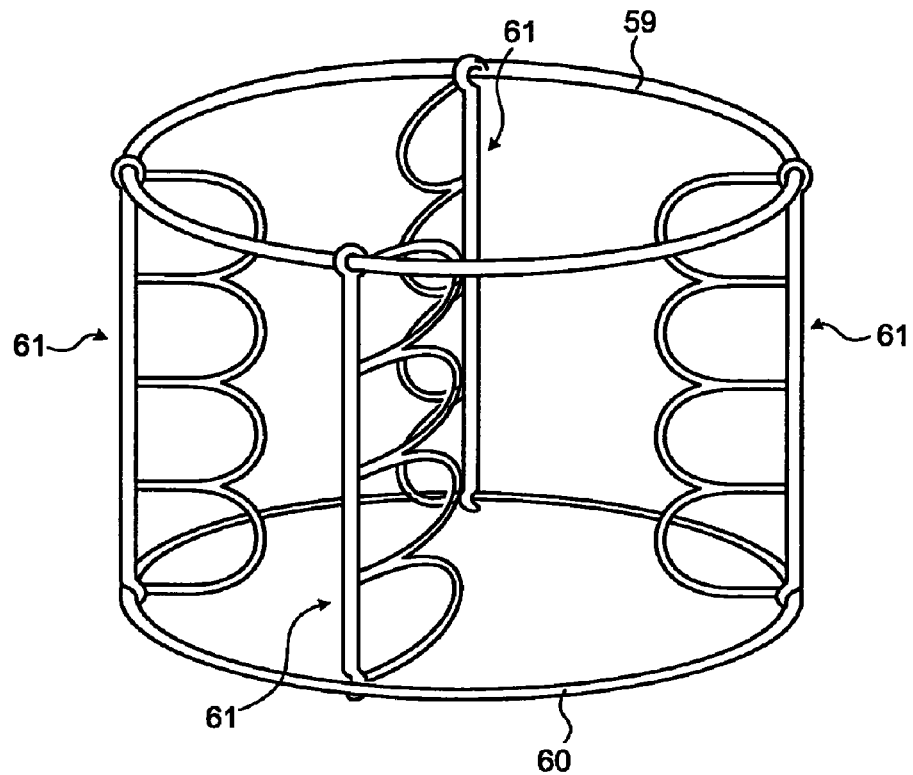
FIG. 15 is a schematic diagram showing the construction of a holder constructing an endoscope sterilizing test pack according to Modification Example 3 of the second embodiment.

Modification Example 3 of the second embodiment will be described. As in Modification Example 2, an endoscope sterilizing test pack according to Modification Example 3 has holders spirally holding the tube housing unit 27. FIG. 15 is a schematic diagram showing the entire construction of such holders. As shown in FIG. 15, the holders used in Modification Example 3 spirally hold the tube housing unit 27 by inserting the tube housing unit 27 into hole portions formed in holding units 61 arranged between an upper ring member 59 and a lower ring member 60.

Figure 16:
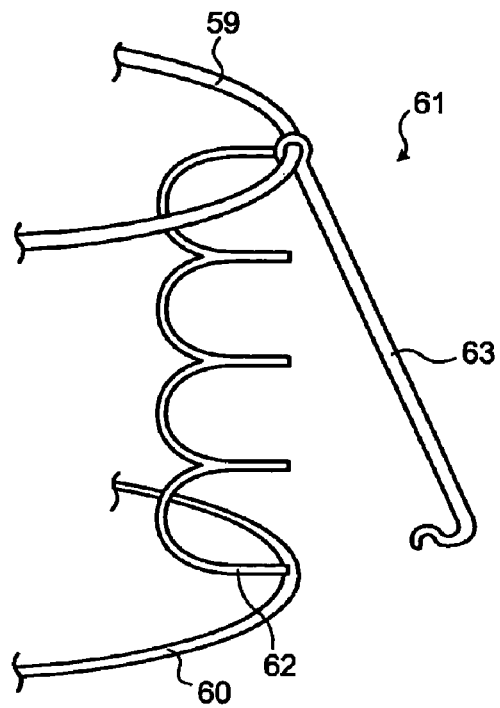
FIG. 16 is a partially enlarged view of the holder.

FIG. 16 is a schematic diagram showing the construction of the holding unit 61. As shown in FIG. 16, the holding unit 61 has a housing member 62 having a construction in which respective ends are fixed to the upper ring member 59 and the lower ring member 60 and U-shaped constructions are arranged between two ends at a predetermined pitch, and a retaining member 63 formed of a rod-like member having one end rotatably fixed to the upper ring member 59 and the other end formed to be removable from the lower ring member 60.

In Modification Example 3, the tube housing unit 27 is held as follows. The tube housing unit 27 is suitably and spirally arranged in the U-shaped constructions formed in the housing member 62 in the state that the retaining member 63 is removed from the lower ring member 60 (that is, the state shown in FIG. 16). The other end of the retaining member 63 is then fixed to the lower ring member 60. The opening sides of the U-shaped constructions are closed to prevent the tube housing unit 27 from being removed from the U-shaped constructions. The held state of the tube housing unit 27 is established. As in Modification Example 2, the tube housing unit 27 is spirally held.

A third embodiment will be described. An endoscope sterilizing test pack according to the third embodiment employs a construction in which a tube is held in a predetermined closed case to maintain the inside of such case in substantially vacuum atmosphere at sterilizing gas admission.

Figure 17:
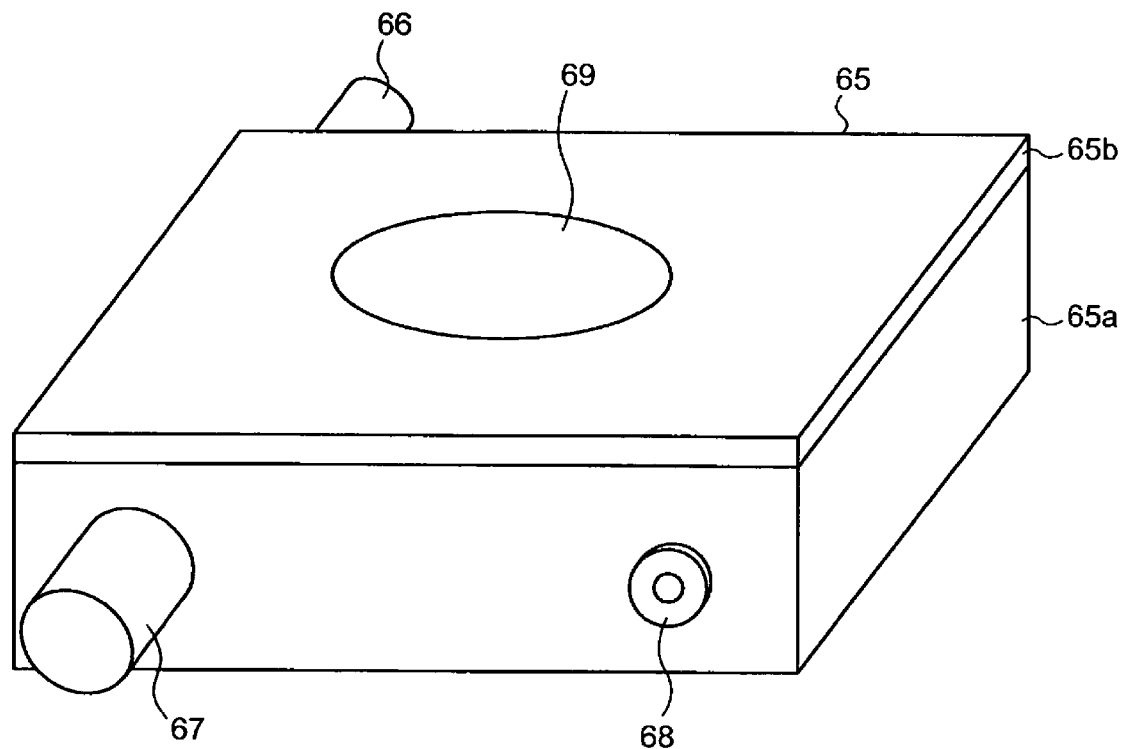
FIG. 17 is a schematic diagram showing an appearance of an endoscope sterilizing test pack according to a third embodiment.

FIG. 17 is a schematic diagram showing an appearance of the endoscope sterilizing test pack according to the third embodiment. As shown in FIG. 17, the endoscope sterilizing test pack according to the third embodiment has a case 65 housing a tube, a check valve 66 changing the inner space of the case 65 into substantially vacuum atmosphere, a cap 67 housing the inner case in its inside and functioning as an example of a sheath member in the scope of the claims together with the case 65, a gas admission unit 68 admitting the sterilizing gas into the tube, and a soft sheet 69 detecting whether or not the inner space of the case 65 is maintained in substantially vacuum atmosphere.

Figure 18:
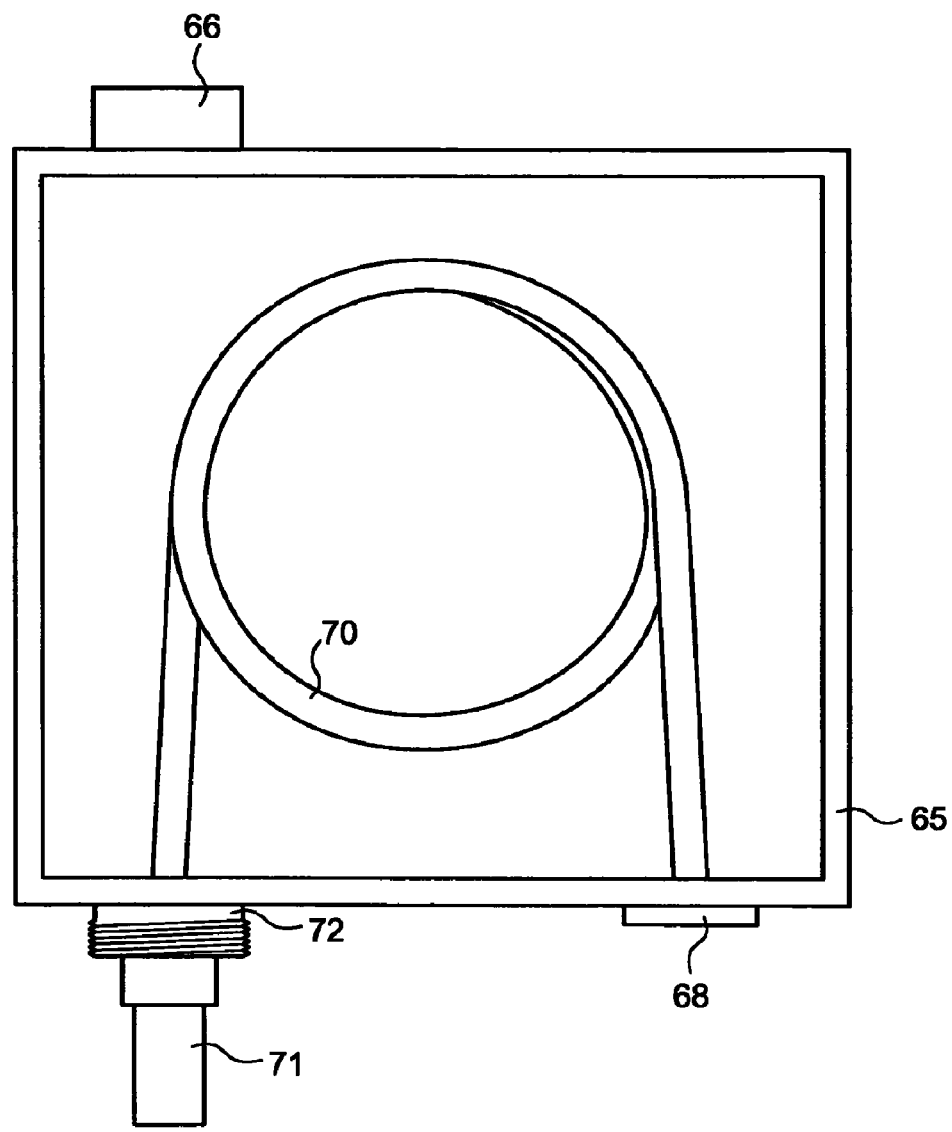
FIG. 18 is a schematic diagram showing the construction of the endoscope sterilizing test pack according to the third embodiment.

FIG. 18 is a schematic diagram showing the construction of the endoscope sterilizing test pack according to the third embodiment. As shown in FIG. 18, a tube 70 is arranged in the case 65, and an inner case 71 and a connection unit 72 for communicating the tube 70 with the inner case 71 are arranged on the outside of the case 65 and in a region blocked from the outer space by the cap 67 during use. In the endoscope sterilizing test pack according to the third embodiment having the above construction, the sterilizing gas inputted from the outer space through the gas admission unit 68 is admitted through the tube 70 into the inner case 71.

Figure 19:
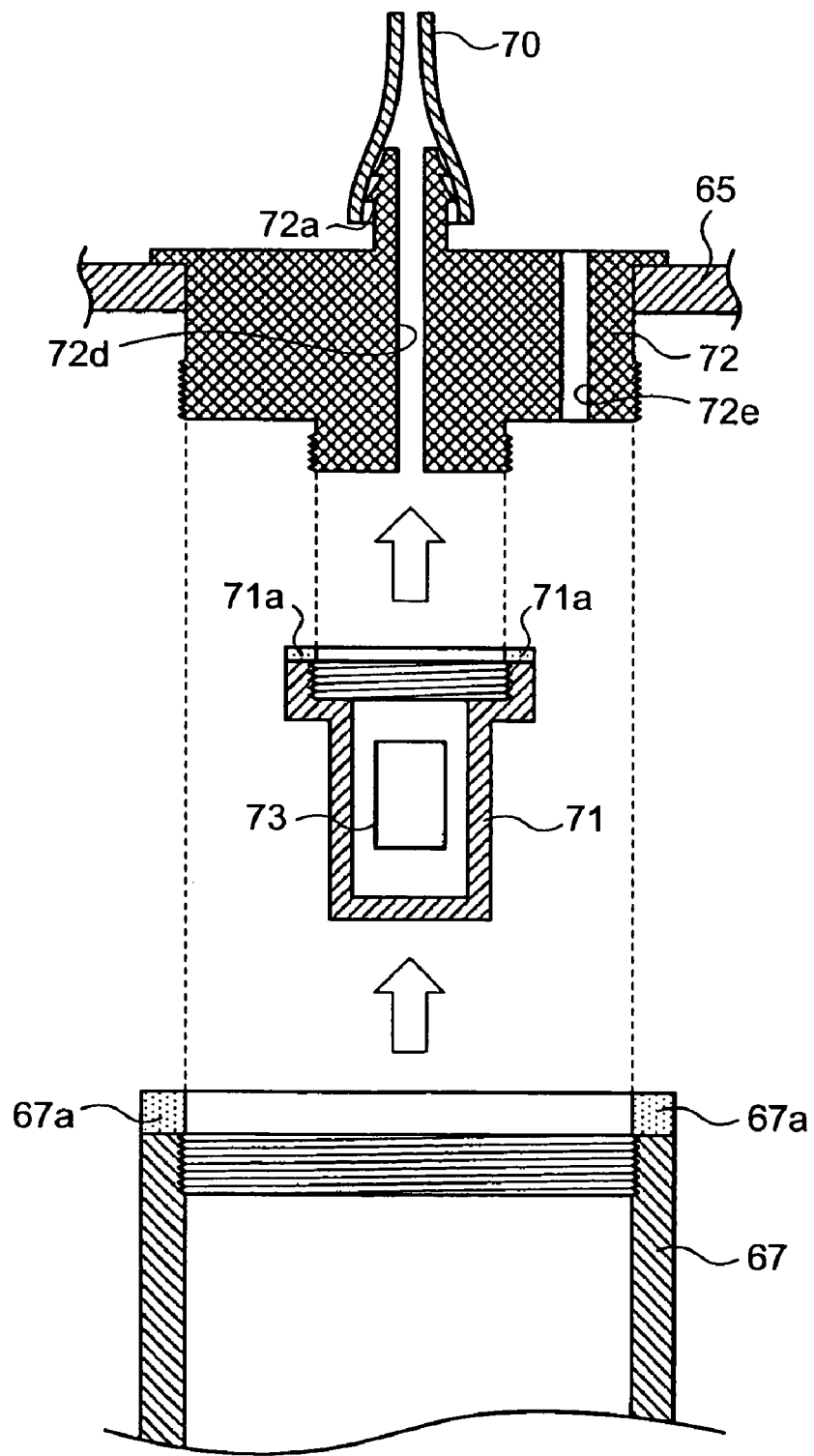
FIG. 19 is a schematic diagram showing the construction of a cap, an inner case, and a connection unit.

The construction of the cap 67, the inner case 71, and the connection unit 72 will be described in detail. FIG. 19 is a schematic diagram showing the construction of the cap 67, the inner case 71, and the connection unit 72. The cap 67 blocks the inner case 71 from the outer space and has the function of substantially hermetically blocking the periphery of the inner case 71 from the outer space through both the vacuum drawing process and the sterilizing gas admission process in the sterilization treatment. Specifically, the cap 67 has an opening formed on the side connected to the connection unit 72, is formed near such opening with a screw groove for thread jointing the cap 67 to the connection unit 72, and has a seal member 67a arranged in the portion contacted with the case 65.

The seal member 67a is formed of a member which is easy to deform, e.g., an elastic member and is formed in a ring shape to cover the circumferential edge of the opening of the cap 67. The seal member 67a is arranged in the portion contacted with the case 65. When the cap 67 is thread jointed to the connection unit 72, the cap 67 can be substantially hermetically fixed to the case 65. The inner space of the cap 67, that is, the periphery of the inner case 71 can be blocked from the outer space.

The inner case 71 holds an indicator 73 for checking a sterilization effect. The inner case 71 has in its inside a space region holding the indicator 73, is formed with a screw groove for thread jointing the inner case 71 to the connection unit 72, and has a seal member 71a arranged in the portion contacted with the connection unit 72 when the inner case 71 is thread jointed to the connection unit 72. When the inner case 71 having the seal member 71a is thread jointed to the connection unit 72, the portion contacted with the connection unit 72 is substantially hermetically contacted therewith. The manner of hermetical connection of the cap 67 to the case 65 (and the connection unit 72) and the manner of hermetical connection of the inner case 71 to the connection unit 72 may be such that an O-ring of an elastic member is provided in the portion to be hermetically sealed and is deformed in thread joint to contact the respective members therewith.

Figure 20:
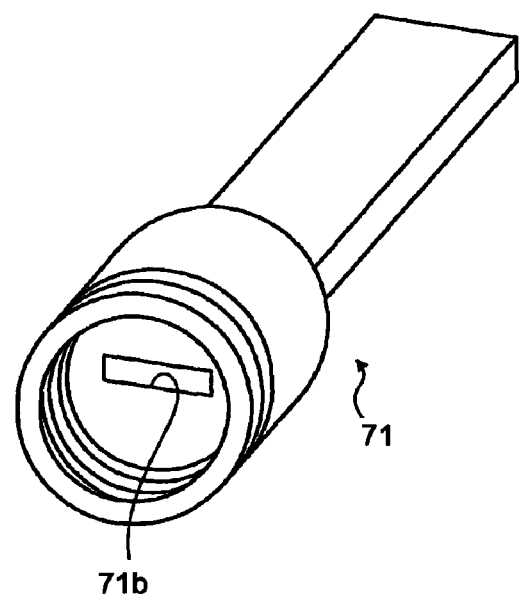
FIG. 20 is a schematic diagram showing an appearance of the inner case.

FIG. 20 is a schematic diagram showing an appearance of the inner case 71. As shown in FIG. 20, the inner case 71 is formed with a slit 71b for inserting and removing the indictor 73 near the region formed with a screw groove, as in the inner case 33 of the second embodiment. A portion housing the sheet-like indicator 73 is formed in a plate shape.

The connection unit 72 has the function of communicating the inner space of the tube 70 with the inner space of the inner case 71 and of communicating the periphery of the inner case 71, that is, the inner space of the cap 67 with the inner space of the case 65. Specifically, as shown in FIG. 19, the connection unit 72 is formed with a connecting protrusion 72a of a shape which can be inserted into the end of the tube 70. In the connection unit 72, the connecting protrusion 72a is substantially hermetically inserted into and fixed to the end of the tube 70. The tube 70 may be substantially hermetically fixed to the connecting protrusion 72a by an adhesive. The connection unit 72 is formed with a throughhole 72d communicating the inside of the tube 70 with the inner space of the inner case 71 when the inner case 71 is thread jointed to the connection unit 72, and a throughhole 72e communicating the inner space of the cap 67 with the inner space of the case 65 when the cap 67 is thread jointed to the connection unit 72. The connection unit 72 having the above construction admits the sterilizing gas passed through the tube 70 into the inner case 71 and has the function of maintaining the pressure of the inner space of the cap 67 to the same value as that of the pressure of the inner space of the case 65, as described later.

Figure 21:
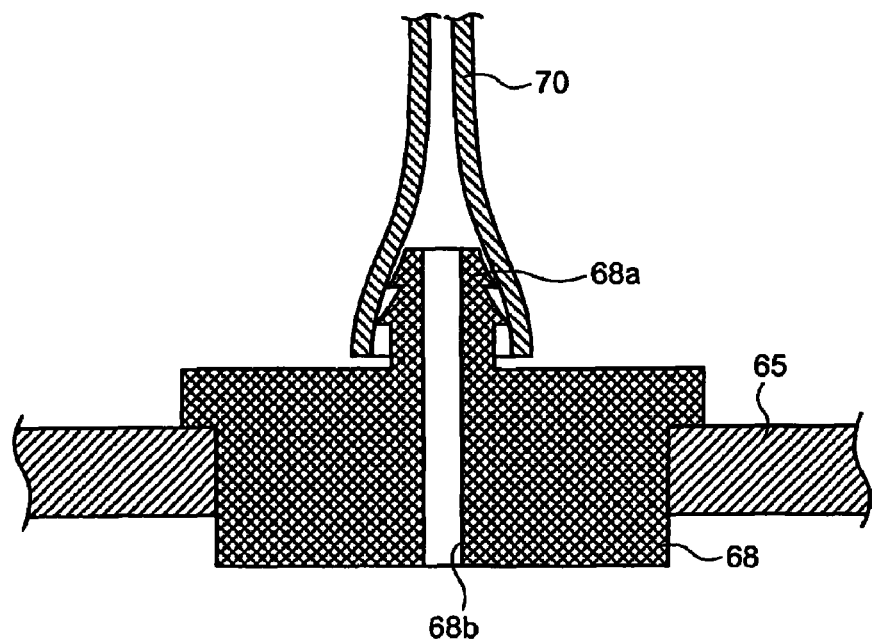
FIG. 21 is a schematic diagram showing the construction of a gas admission unit.

The gas admission unit 68 will be described. FIG. 21 is a schematic diagram showing the construction of the gas admission unit 68. As shown in FIG. 21, the gas admission unit 68 is formed with a connecting protrusion 68a having a shape which can be inserted into the end of the tube 70 (the end opposite the side connected to the connection unit 72), and a throughhole 68b for communicating the tube 70 with the outer space in the state that the connecting protrusion 68a is inserted into the end of the tube 70. The tube 70 is substantially hermetically fixed to the connecting protrusion 68a. Both may be substantially hermetically fixed by an adhesive. The throughhole 68b is formed so that the tube 70 is communicated with the outer space. At sterilizing gas admission, the sterilizing gas can be admitted from the outer space to be admitted into the inner case 71. The diameter of the throughhole 68b formed in the gas admission unit 68 is preferably substantially the same value as that of the inner diameter of the tube 70. Needless to say, the tube 70 has a duct construction similar to the duct in the endoscope. The inside of the case 65 may be contacted or non-contacted with the tube 70 unless temperature rise of the tube 70 and the passing of the sterilizing gas in the tube 70, i.e., the sterilization effect is affected.

Figure 22:
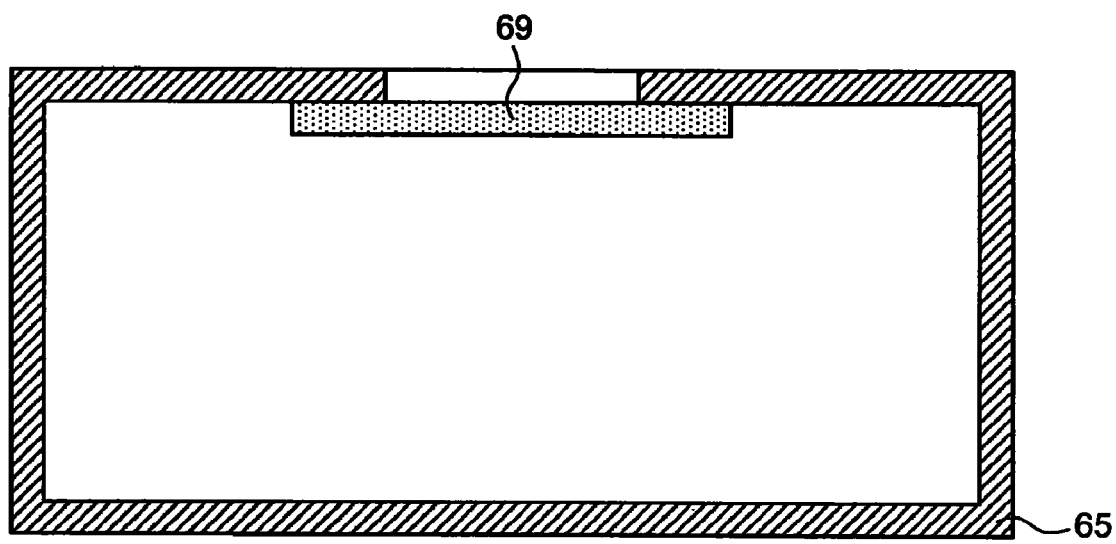
FIG. 22 is a schematic diagram showing the construction of a soft sheet.

The soft sheet 69 will be described. As in the soft sheet 56 of the second embodiment, the soft sheet 69 detects whether or not the inner space of the case 65 is maintained in substantially vacuum atmosphere. FIG. 22 is a schematic diagram showing the construction of the soft sheet 69. As shown in FIG. 22, the case 65 (in this embodiment, the top of a cap 65b shown in FIG. 17) is formed with a predetermined opening. The soft sheet 69 covering such opening is substantially hermetically fixed to the case 65. The soft sheet 69 is formed of a flexible sheet-like member having hermeticity and has a characteristic in which its shape is changed according to the magnitude relation between the pressure in the outer space and the pressure in the inner space of the case 65.

Figure 23:
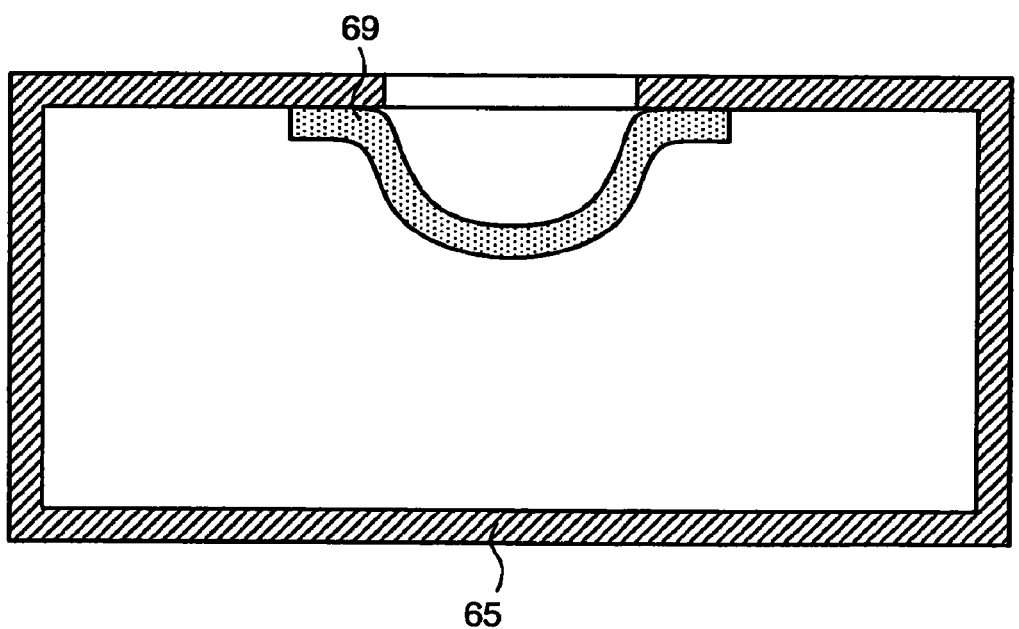
FIG. 23 is a schematic diagram showing the state of the soft sheet when the endoscope sterilizing test pack according to the third embodiment is taken out from a sterilizer.

FIG. 23 is a schematic diagram showing the state of the soft sheet 69 when the endoscope sterilizing test pack according to the third embodiment is taken out from the sterilizer. The endoscope sterilizing test pack according to the third embodiment is designed so that the inside of the chamber of the sterilizer is vacuum drawn to change the inner space of the case 65 (and the inner space of the cap 67) into substantially vacuum atmosphere. When the endoscope sterilizing test pack functions as designed, the pressure in the outer space as an atmospheric pressure has a value higher than that of the pressure in the inner space of the case 65 maintained in substantially vacuum atmosphere and the shape of the soft sheet 69 is changed into a concave shape, seen from the outer space, as shown in FIG. 23. The user visually checks the shape of the soft sheet 69 and can easily determine whether or not the inner space of the case 65 is maintained in substantially vacuum atmosphere. The check valve 66 has the same construction as that of the check valve 28 of the second embodiment and is substantially hermetically adhered and fixed to the case 65. Needless to say, the case 65 is constructed of a case body 65a and the cap 65b which are substantially hermetically adhered and fixed to each other, and is formed of a construction and material (metal material, resin material, and so on) which cannot be deformed due to change in pressure in the sterilizer.

Figure 24:
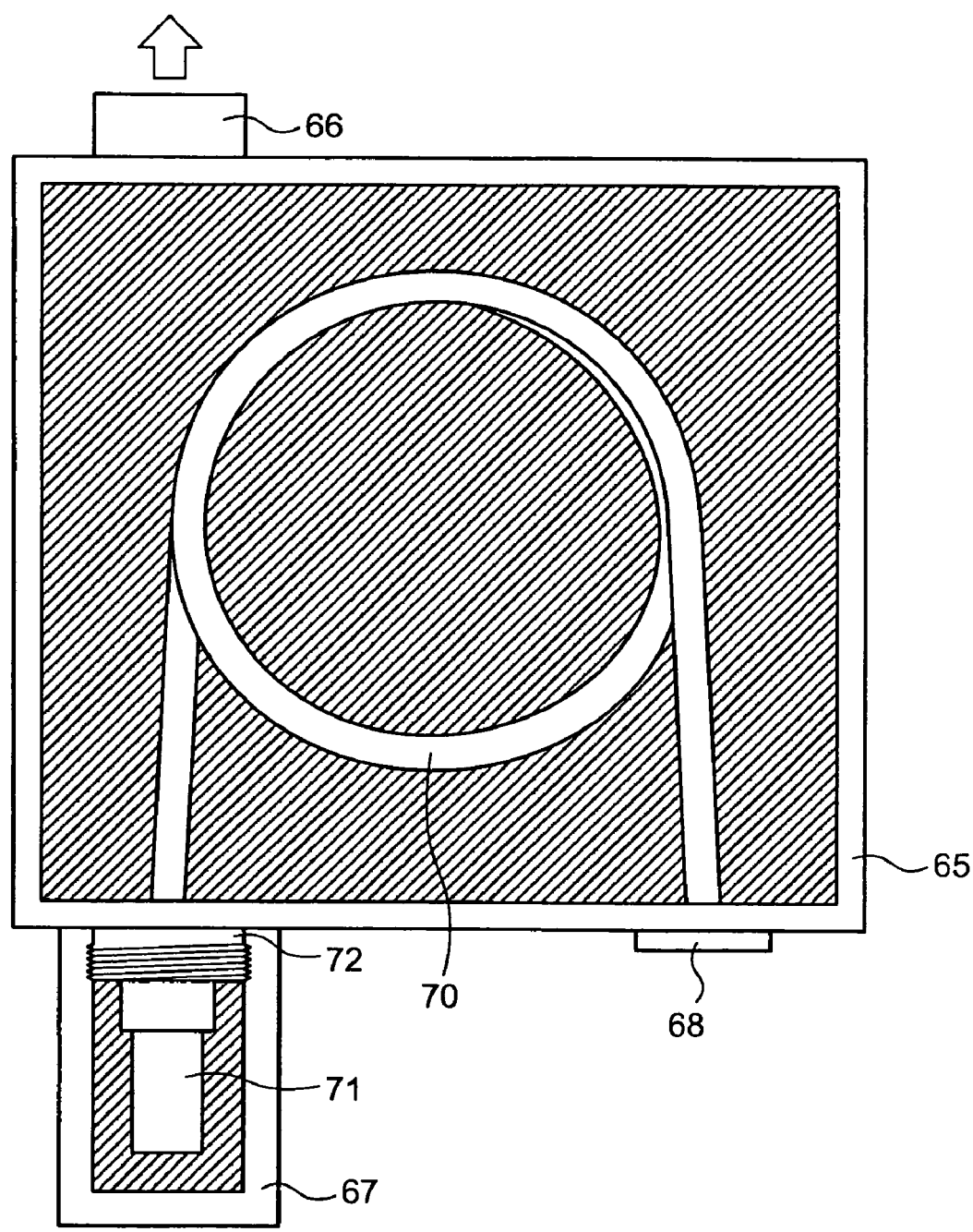
FIG. 24 is a schematic diagram of assistance in explaining the operation of the endoscope sterilizing test pack according to the third embodiment.

The operation of the endoscope sterilizing test pack according to the third embodiment will be described with reference to FIG. 24. As in First and Second Embodiments, the endoscope sterilizing test pack according to the third embodiment is introduced into the sterilizer together with the endoscope and the inside of the chamber of the sterilizer is vacuum drawn to admit the sterilizing gas. When such vacuum drawing process is performed in the third embodiment, the operation of the check valve 66 changes the peripheries of the tube 70 and the inner case 71 into substantially vacuum atmosphere. Such substantially vacuum atmosphere is maintained at subsequent sterilizing gas admission. As in the check valve 28 of the second embodiment, the check valve 66 is opened when the pressure in the case 65 is higher than the pressure in the outer space. When the pressure in the outer space is lowered in the vacuum drawing process, the gas remained in the inner space of the case 65 is discharged to the outer space, the inner space is changed into substantially vacuum atmosphere, in other words, the periphery of the tube 70 is changed into substantially vacuum atmosphere.

As already described, the connection unit 72 is formed with the throughhole 72e for communicating the inner space of the cap 67 with the inner space of the case 65. In the state that the cap 67 is connected to the connection unit 72, the pressure in the inner space of the cap 67 maintains the same value as that of the pressure in the inner space of the case 65. The operation of the check valve 66 changes the inner space of the case 65 into substantially vacuum atmosphere. The inner space of the cap 67 is changed into substantially vacuum atmosphere. The periphery of the inner case 71 is changed into substantially vacuum atmosphere. As in the second embodiment, at sterilizing gas admission, the peripheries of the tube 70 and the inner case 71 are maintained in substantially vacuum atmosphere.

An advantage of the endoscope sterilizing test pack according to the third embodiment will be described. As in First and Second Embodiments, the endoscope sterilizing test pack according to the third embodiment uses the tube having the same construction as that of the duct provided in the endoscope and can determine the sterilized state of the endoscope sterilized.

The endoscope sterilizing test pack according to the third embodiment has a simplified appearance construction and can be easily handled. As shown in FIG. 17, the appearance of the endoscope sterilizing test pack according to the third embodiment has a box shape and can be carried in and out from the sterilizer more easily. When such appearance construction is realized, the reliability of determination of the sterilized state of the endoscope sterilized would not be lowered. As explained in the second embodiment, when the sterilizing gas is admitted in the state that the peripheries of the inner case 71 and the tube 70 are maintained in substantially vacuum atmosphere, heat transmission via the case 65 and the cap 67 need not be considered. An optional specific shape can be employed.

Figure 25:
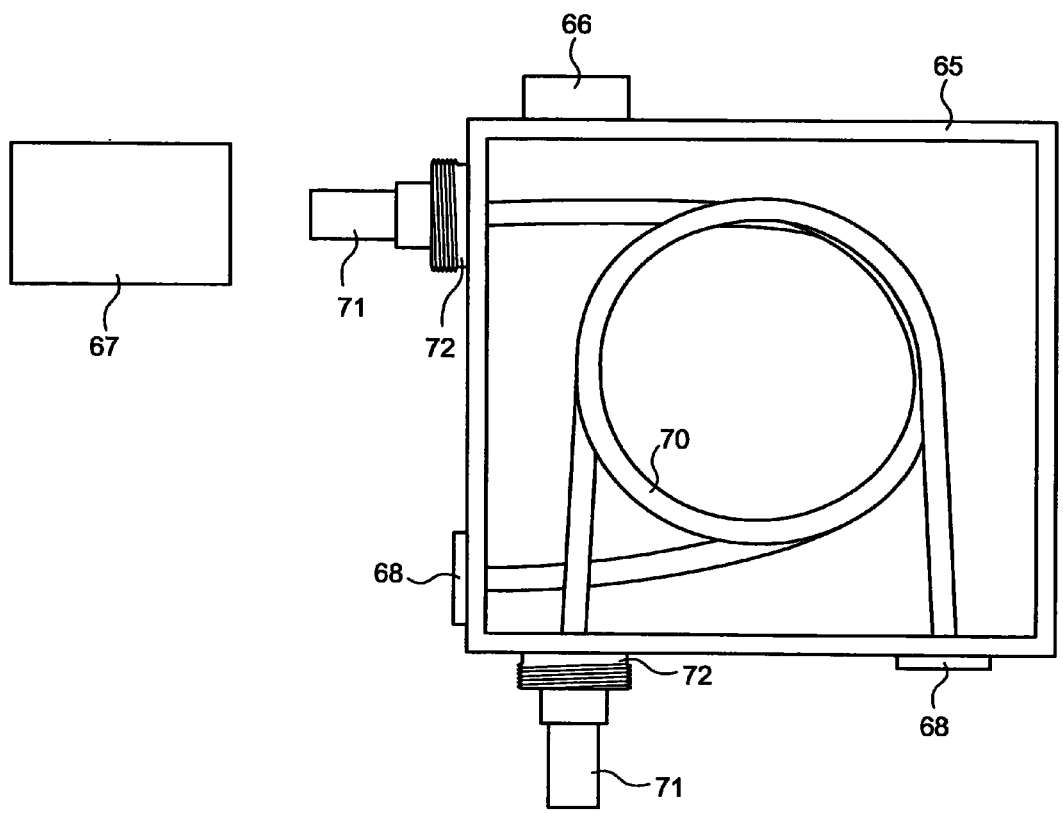
FIG. 25 is a schematic diagram showing a modification example of the third embodiment.

In the third embodiment, as shown in FIG. 25, a plural pairs of the caps 67, the gas admission units 68, the tubes 70, the inner cases 71, and the connection units 72 may be arranged in the single case 65. In such construction, the single endoscope sterilizing test pack can determine the sterilized states of plural kinds of endoscopes. In the third embodiment, the sterilizing gas is admitted through the single tube 70 into the inner case 71. The present invention is not limited to such construction. As in the second embodiment, the sterilizing gas may be admitted through plural tubes into the inner case 41. In the third embodiment, the soft sheet 69 is provided in part of the case 65 to check whether or not the inside of the case 65 is maintained in substantially vacuum atmosphere.

The construction of the gas detection unit 35 as shown in the second embodiment may be provided in the cap 67. Then, the sterilizing gas entry into the inside (that is, whether or not substantially vacuum atmosphere is maintained) can be checked. The soft sheet 69 can be omitted.

An endoscope sterilizing test pack according to a fourth embodiment will be described. The endoscope sterilizing test pack according to the fourth embodiment has a construction in which an outer case housing a tube is formed to be opened and closed and the tube and an inner case can be replaced when the outer case is opened.

Figure 26:
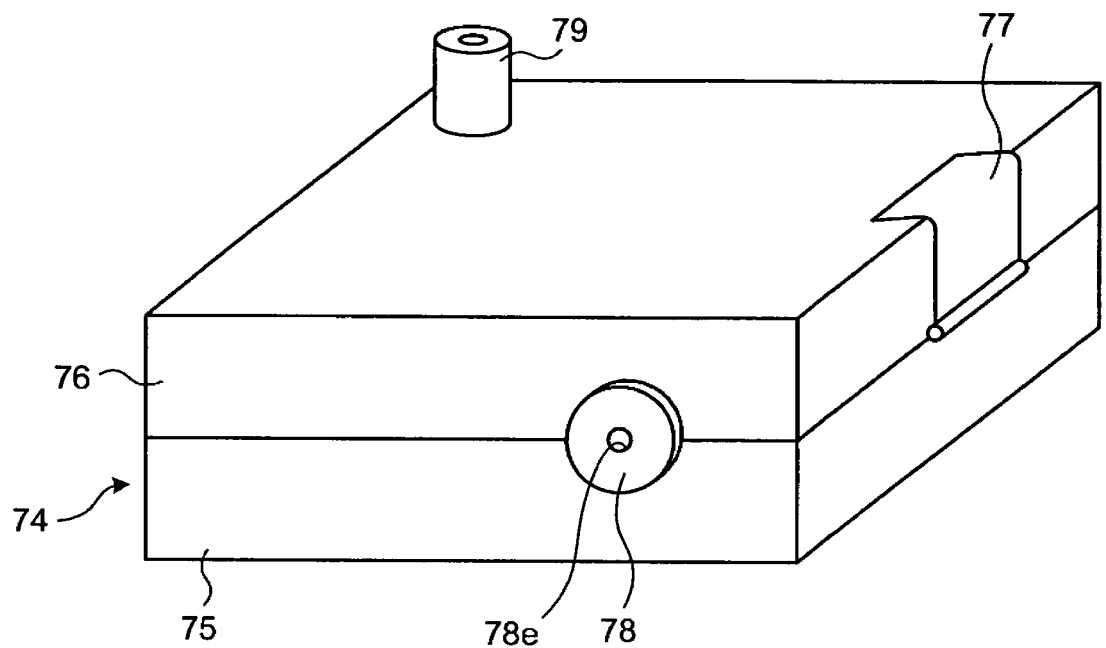
FIG. 26 is a schematic diagram showing an appearance of an endoscope sterilizing test pack according to a fourth embodiment.

FIG. 26 is a schematic diagram showing an appearance of the endoscope sterilizing test pack according to the fourth embodiment. As shown in FIG. 26, the endoscope sterilizing test pack according to the fourth embodiment has a case 74 constructed of a lower case 75 and an upper case 76 formed to be separable from each other, a retainer 77 arranged and fixed to the lower case 75 and retaining the upper case 76 when the case 74 is closed, a gas admission unit 78 arranged to be fitted in concave portions formed in the lower case 75 and the upper case 76 and having a gas admission port 78e communicated with a tube 80 (not shown in FIG. 26) arranged in the case 74, and a check valve 79 for changing the inner space of the case 74 into substantially vacuum atmosphere.

Figure 27:
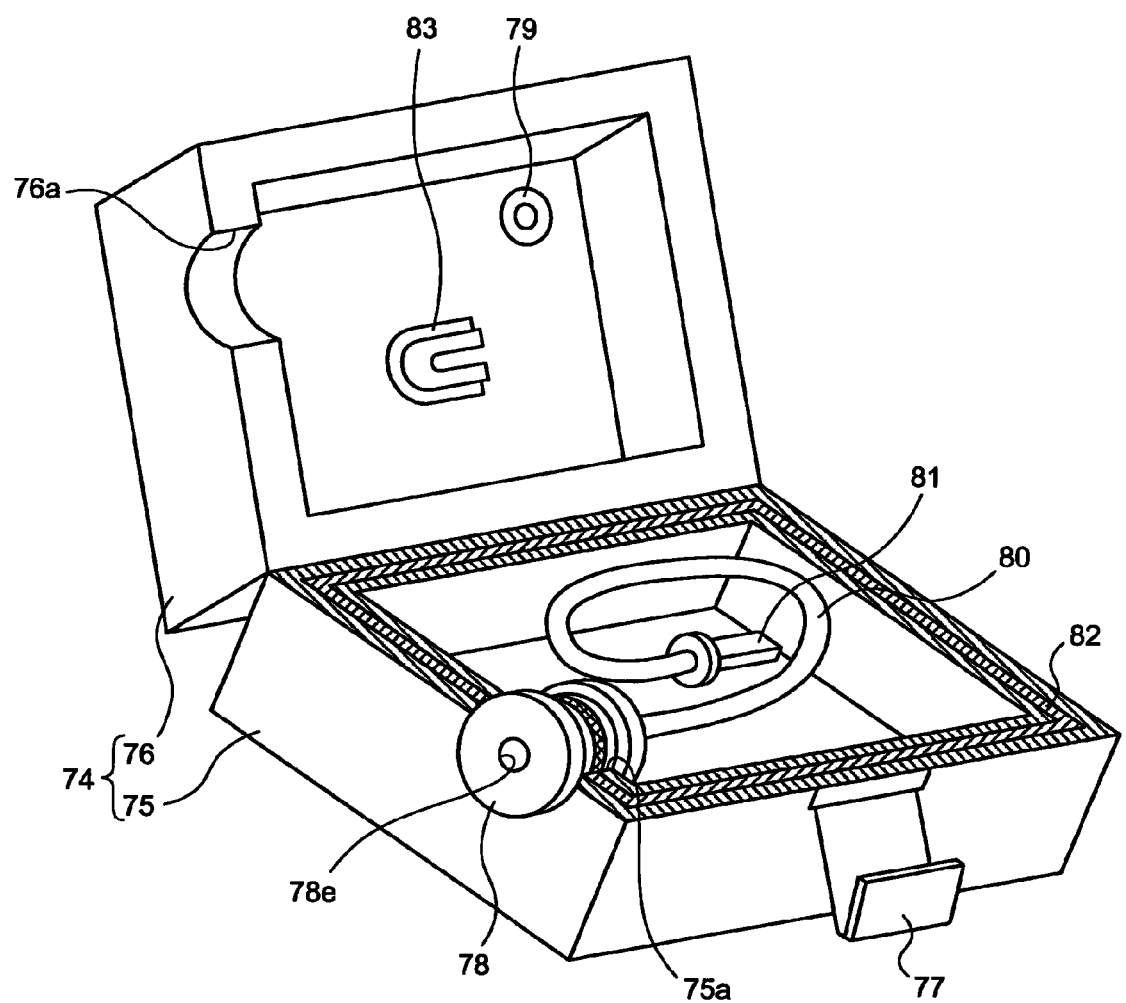
FIG. 27 is a schematic diagram showing an appearance of the endoscope sterilizing test pack when a case is opened.

FIG. 27 is a schematic diagram showing an appearance of the endoscope sterilizing test pack when the case 74 is opened. As shown in FIG. 27, the tube 80 and an inner case 81 are arranged in the lower case 75 to be communicated with the gas admission unit 78. A gas detection unit 83 detecting the presence or absence of leakage of the sterilizing gas is arranged on the inner surface of the upper case 76. The lower case 75 and the upper case 76 are formed with concave portions 75a and 76a, respectively, for fitting the gas admission unit 78 therein. A seal member 82 is arranged on the surface of the lower case 75 contacted with the upper case 76 so that the portions of the lower case 75 and the upper case 76 contacted with each other are substantially hermetical when the case 74 is closed.

Figure 28:
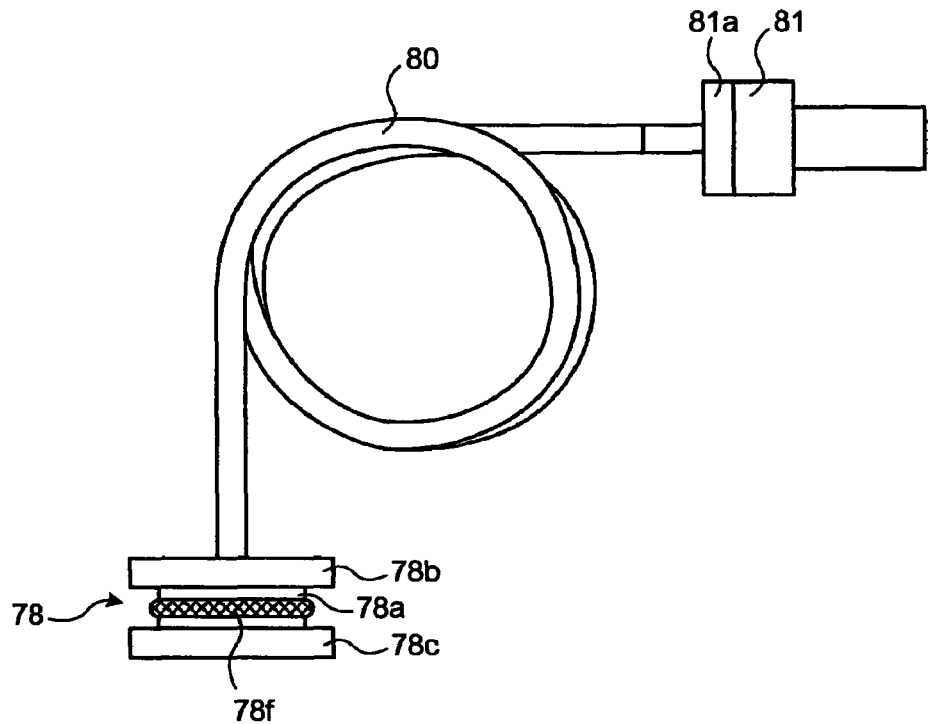
FIG. 28 is a schematic diagram showing the connection relation between a gas admission unit, a tube, and an inner case.

The gas admission unit 78, the tube 80, and the inner case 81 will be described. FIG. 28 is a schematic diagram showing the connection relation between the gas admission unit 78, the tube 80, and the inner case 81. As shown in FIG. 28, the gas admission unit 78 is sequentially connected to the tube 80 and the inner case 81. The sterilizing gas admitted from the outer space through the gas admission port 78e formed in the gas admission unit 78 passes through the tube 80 to the indicator arranged in the inner case 81. The inner case 81 has a body portion capable of holding the indicator in the inside, and a connection unit 81a removable from the body portion and substantially hermetically fixed to the body portion when being fitted in the body portion. The construction of the body portion is the same as that of the inner case 71 of the third embodiment. The connection unit 81a is substantially hermetically fixed to the tube 80 and has a throughhole communicating the inside of the body portion with the inside of the tube 80. A specific construction of the connection unit 81a is the same as that of later-described connection units 92 and 93.

Figure 29:
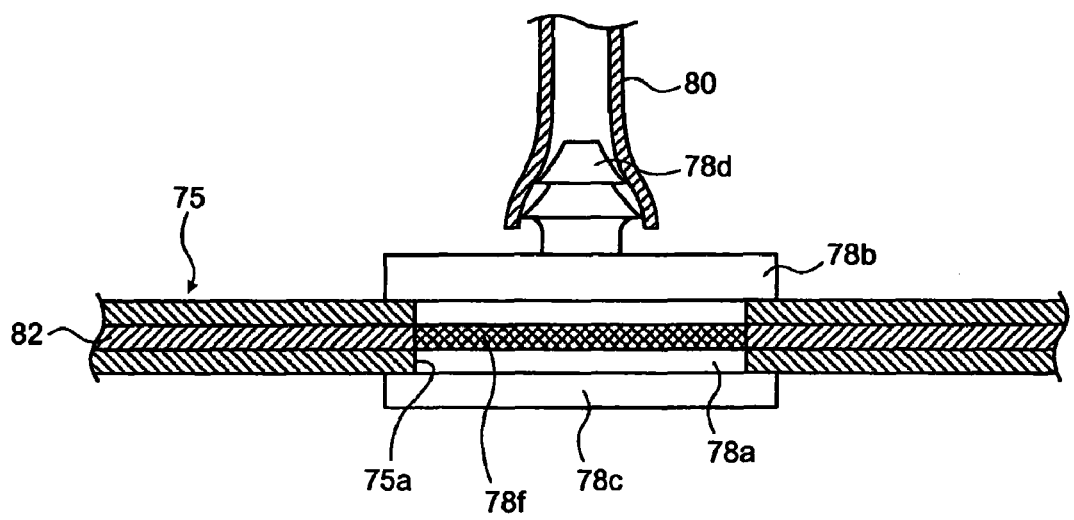
FIG. 29 is a schematic diagram showing the construction of the gas admission unit.

FIG. 29 is a schematic diagram showing the construction of the gas admission unit 78. As shown in FIG. 29, the gas admission unit 78 has a body 78a having a side surface shape corresponding to the shape of the concave portions 75a and 76a, and disk-like members 78b and 78c formed to interpose the body 78a between the upper and lower sides. A connecting protrusion 78d of a shape which can be inserted into the tube 80 and can be hermetically fixed to the tube 80 when being inserted is formed on the disk-like member 78b. The gas admission port 78e is communicated with the edge of the connecting protrusion 78d via the throughhole penetrating through the body 78a and the disk-like members 78b and 78d. Such construction can admit the sterilizing gas in the outer space into the tube 80. An O-ring 78f formed of an elastic material is contacted onto the outer circumference of the body 78a.

The body 78a can be substantially hermetically fitted in the concave portions 75a and 76a. Specifically, the body 78a has a slightly smaller outer diameter than the inner diameter of the throughhole which can be inserted into the inner diameter of the throughhole formed by the concave portions 75a and 76a when the case 74 is closed and is held to be interposed in the inner diameter of the throughhole formed by the concave portions 75a and 76a. The O-ring 78f arranged on the circumference of the body 78a has a larger outer diameter than the throughhole formed by the concave portions 75a and 76a. The O-ring 78f formed of an elastic material is deformed and is contacted along the overall circumference of the inner diameter of the throughhole formed by the concave portions 75a and 76a. In such construction, when the gas admission unit 78 is arranged, the body 78a can be substantially hermetically fixed without a space between the body 78a and the concave portions 75a and 76a. The entire body 78a may be formed of an elastic member. In this case, the outer diameter of the body 78a need to be set to be slightly larger than the inner diameter of the throughhole formed by the concave portions 75a and 76a (in such construction, the O-ring 78f can be omitted). More preferably, only the portions of the body 78a near the portions contacted with the concave portions 75a and 76a may be formed of an elastic member. The penetrated gas admission port 78e may be formed of a hard member. In such construction, only the portions of the body 78a fitted in the concave portions 75a and 76a near the outer circumference are deformed. The initial shape is maintained in the center portion formed with the throughhole to prevent the shape of the throughhole formed in the center portion from being changed. The basic material of the body 78a may be an elastic member and the periphery of the throughhole may be reinforced by a metal member.

Figure 30:
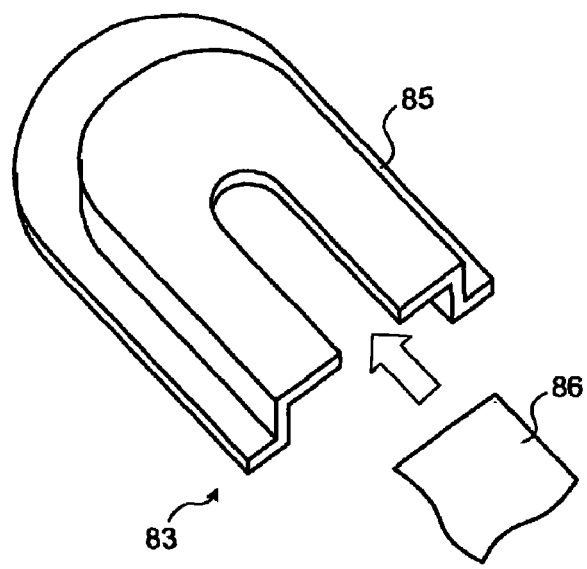
FIG. 30 is a schematic diagram showing the construction of a gas detection unit.

The gas detection unit 83 will be described. FIG. 30 is a schematic diagram showing the construction of the gas detection unit 83. As in the gas detection unit 35 of the second embodiment, the gas detection unit 83 detects whether or not the sterilizing gas has entered the inner space of the case 74. Specifically, the gas detection unit 83 is formed by a housing unit 85 arranged on the inner surface of the upper case 76, and an indicator 86 housed in the housing unit 85. The construction of the check valve 79 is the same as that of the check valve 28 of the second embodiment.

An advantage of the endoscope sterilizing test pack according to the fourth embodiment will be described. As in the advantage of the third embodiment, the endoscope sterilizing test pack according to the fourth embodiment can maintain high reliability of determination of the sterilized state and can open and close the case 74 so that maintenance is easy. When any malfunction is caused, the case 74 is opened to easily inspect the tube 80 and other components housed in the inside. In view of such point, handling is easy.

The endoscope sterilizing test pack according to the fourth embodiment has an advantage with regard to versatility. Specifically, in the fourth embodiment, the case 74 can be opened and closed. When a different endoscope is sterilized, a tube corresponding to the new endoscope is prepared and can be easily replaced with the old tube. The endoscope sterilizing test pack according to the fourth embodiment can respond to endoscopes having various constructions. In view of such point, the endoscope sterilizing test pack according to the fourth embodiment has wide versatility.

A modification example of the fourth embodiment will be described. In the endoscope sterilizing test pack according to this modification example, as in First and Second Embodiments, the endoscope sterilizing test pack according to the fourth embodiment has a construction in which the sterilizing gas is admitted into the inner case through two tubes. This modification example is different from the fourth embodiment only in the gas admission unit, the tubes, and the inner case. Otherwise, this modification example uses the same components as those of the fourth embodiment.

Figure 31:
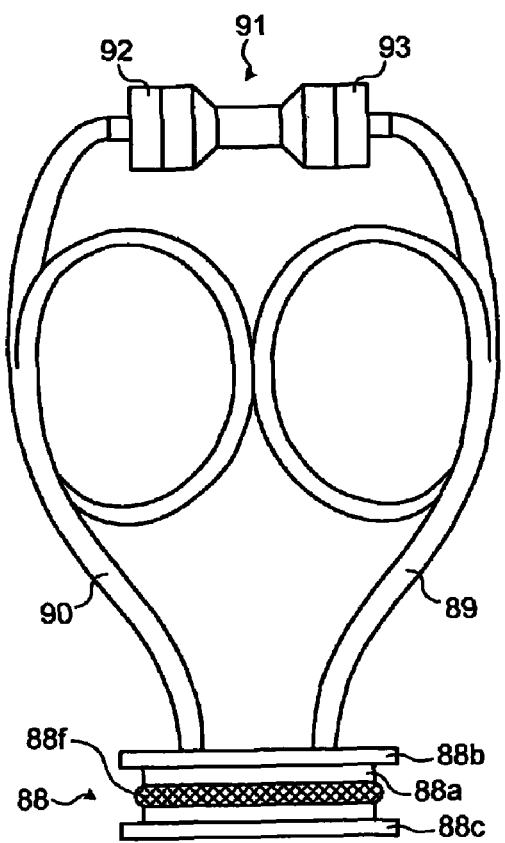
FIG. 31 is a schematic diagram showing an appearance of a gas admission unit, a first tube, a second tube, and an inner case according to a modification example of the fourth embodiment.

FIG. 31 is a schematic diagram showing an appearance of a gas admission unit 88, a first tube 89, a second tube 90, and an inner case 91 of this modification example. As shown in FIG. 31, as in the gas admission unit 78 of the fourth embodiment, the gas admission unit 88 has a body 88a and disk-like members 88b and 88c and is formed with plural gas admission ports, connecting protrusions, and throughholes (not shown in FIG. 31) communicating both corresponding to the first tube 89 and the second tube 90. In this modification example, as in First and Second Embodiments, the first tube 89 and the second tube 90 preferably have the same length. When they have the same length, the region in which the inner case 91 is positioned corresponds to the midpoint of the duct of the endoscope sterilized. This modification example has the same duct construction as that of First and Second Embodiments.

FIG. 32 is a schematic diagram showing the construction of the inner case 91 and the connection units 92 and 93 for connecting the inner case 91 to the first tube 89 and the second tube 90, respectively. As shown in FIG. 32, the connection units 93 and 92 are fixed to the first tube 89 and the second tube 90 in the state that the inside is communicated and are formed with threads for thread jointing the connection units 93 and 92 to the inner case 91. The inner case 91 is formed with screw grooves corresponding to such threads and has seal members 91b and 92b arranged in the portions contacted with the connection units 92 and 93 to be substantially hermetical when the inner case 91 is thread jointed to the connection units 92 and 93. By using a member of such construction, as in First and Second Embodiments, the endoscope sterilizing test pack according to the fourth embodiment can realize a construction in which the sterilizing gas is admitted into the inner case through plural tubes.

Figure 33:
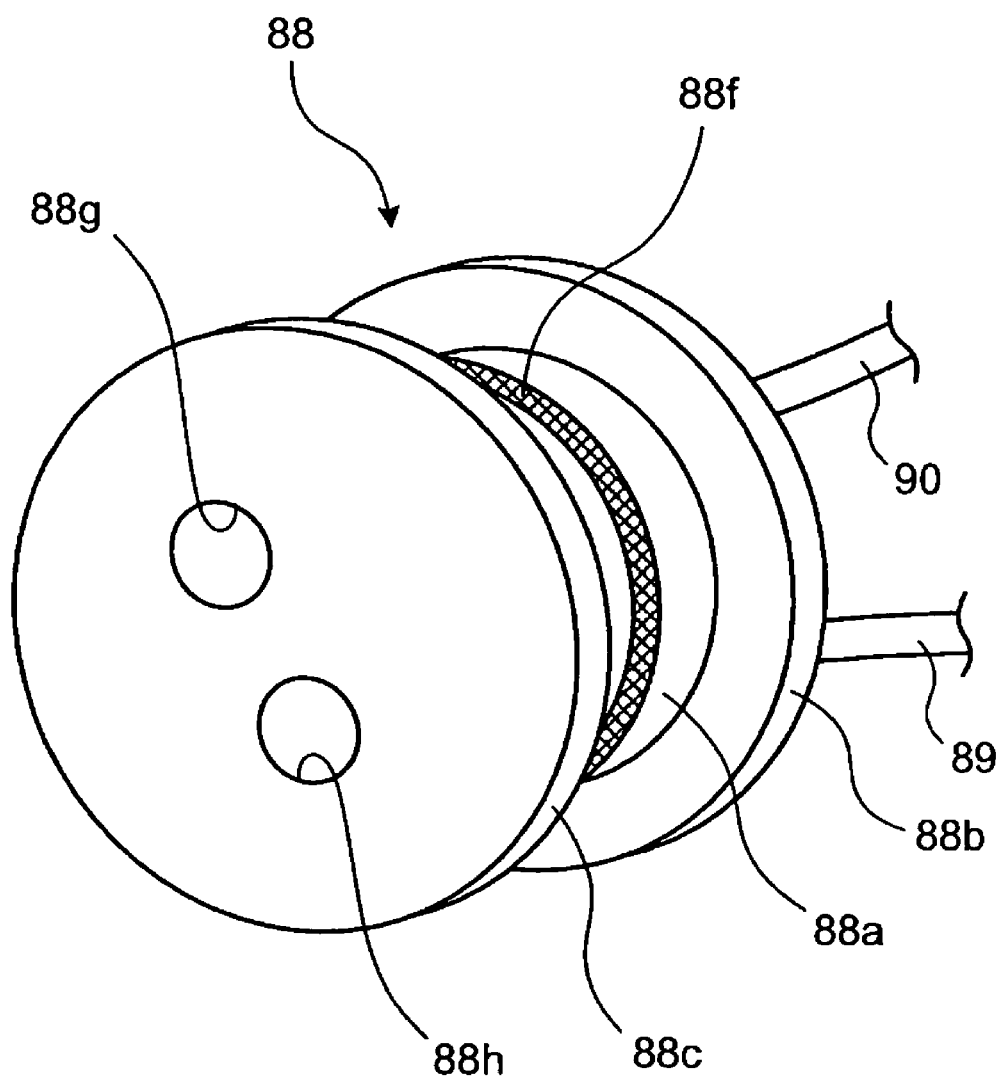
FIG. 33 is a schematic diagram showing an appearance of the gas admission unit.

FIG. 33 is a schematic diagram showing an appearance of the gas admission unit 88. The gas admission unit 88 has an O-ring 88f arranged on the circumference of the body 88a and is formed with gas admission ports 88g and 88h for admitting the sterilizing gas into the first tube 89 and the second tube 90.

Figure 34:
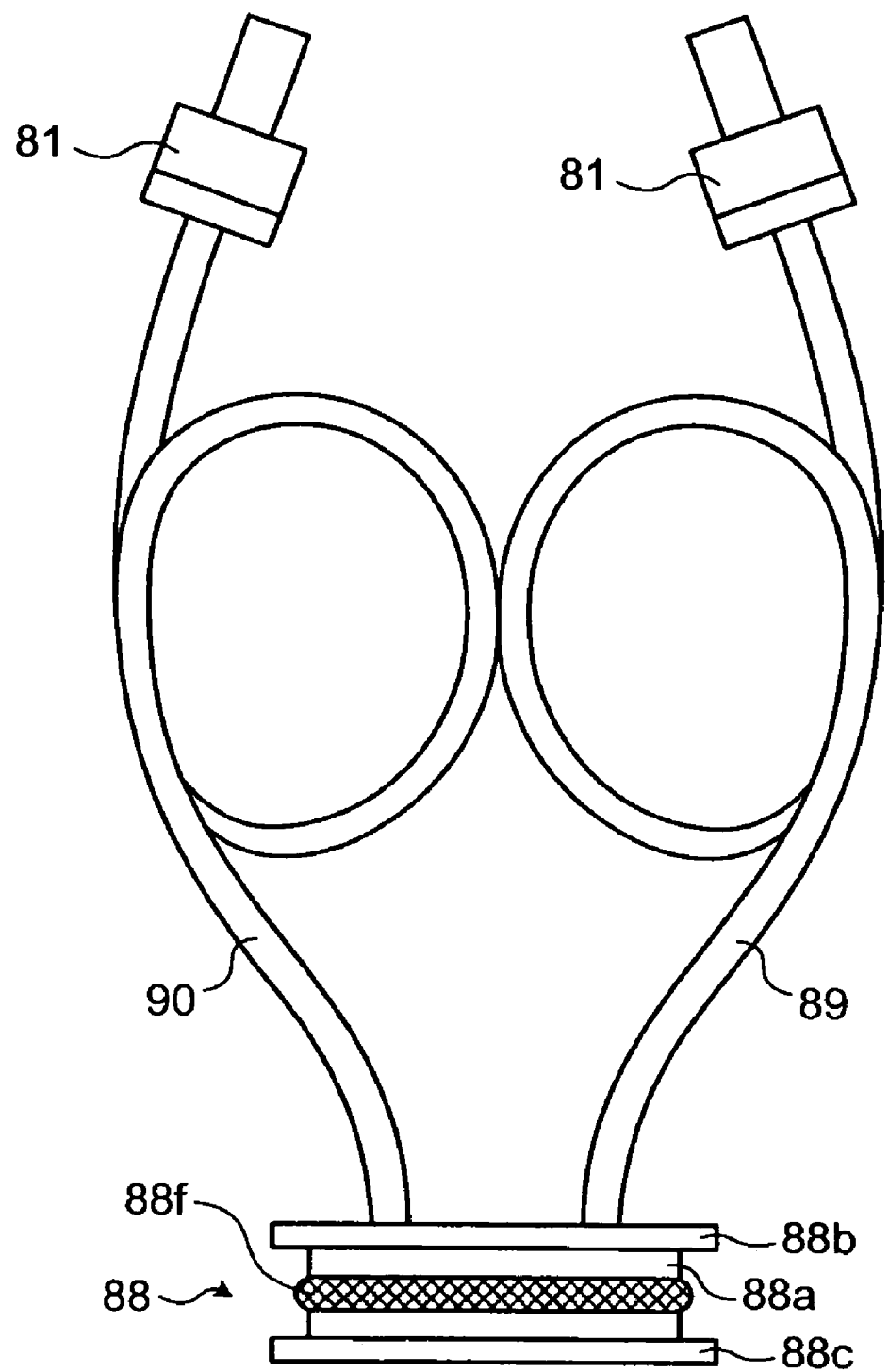
FIG. 34 is a schematic diagram showing another modification example of the fourth embodiment.

In this modification example, the sterilizing gas is admitted into the single inner case through plural tubes. Alternatively, as shown in FIG. 34, plural inner cases may be arranged corresponding to provision of plural tubes and the sterilizing gas may be admitted into each of the inner cases through the single tube. In this case, the single endoscope sterilizing test pack can determine the sterilized states of plural kinds of endoscopes.

Figure 35:
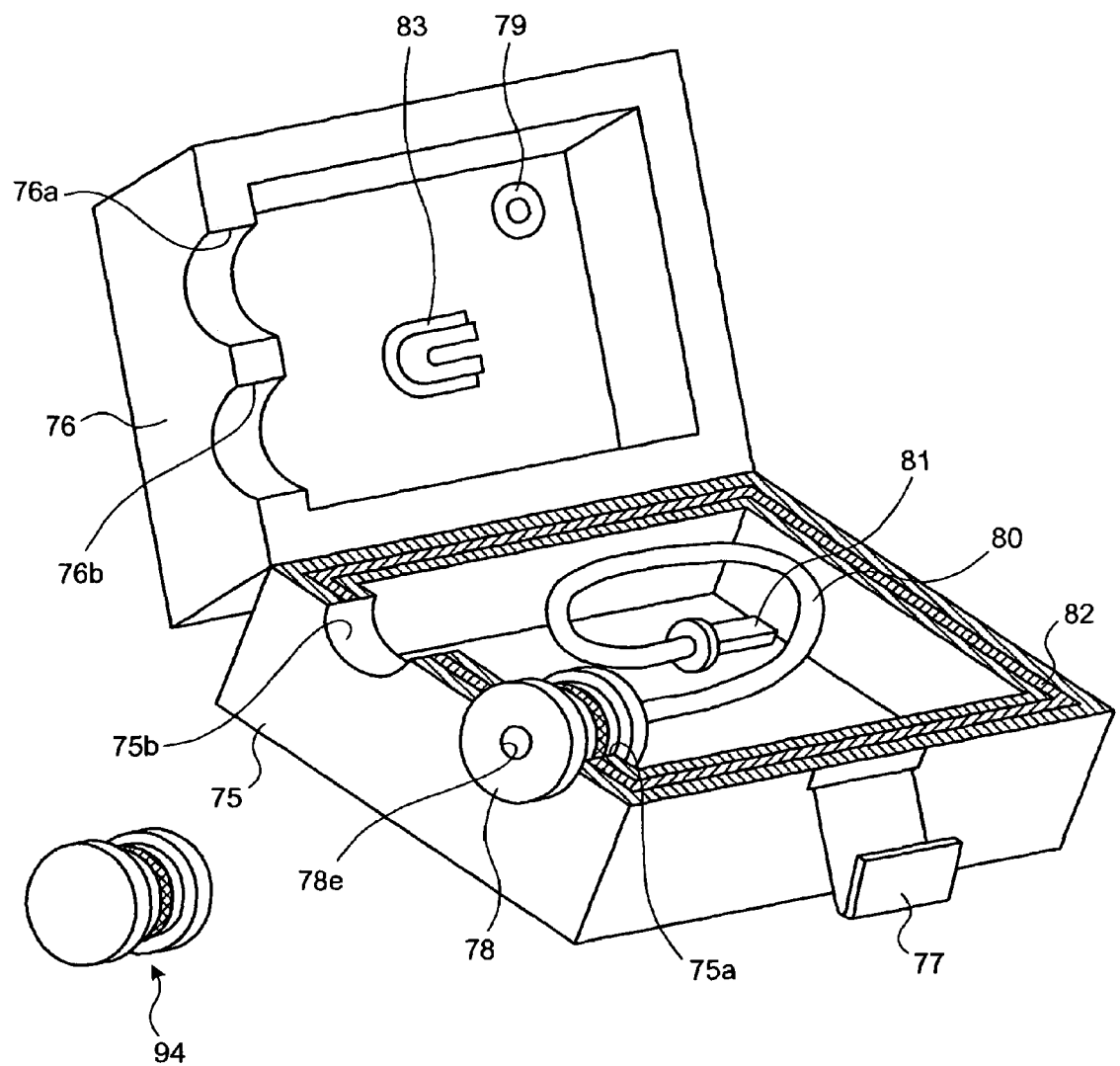
FIG. 35 is a schematic diagram showing a further modification example of the fourth embodiment.

As shown in FIG. 35, the endoscope sterilizing test pack may have concave portions 75a and 76a and may use plural corresponding gas admission units 78 and tubes 80. When such construction is employed, the sterilized states of plural kinds of endoscopes can be determined at the same time. When the endoscope sterilizing test pack having the concave portions 75a and 76a uses only one gas admission unit 78, a predetermined packing is arranged in the concave portions 75a and 76a not used for fitting the gas admission unit 78 therein to secure a substantially hermetical state.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope sterilizing test pack comprising:
an inner case configured for insertion of an indicator for checking a sterilization effect of sterilization treatment;
at least one tube connected to the inner case so that one end is opened and another end is in communication with an inside of the inner case;
an outer case housing the inner case and a part of the tube; and
a tube housing unit in communication with the outer case and configured to have a remaining portion of the tube inserted therethrough;
wherein the tube housing unit has a first and a second flexible pipe substantially hermetically connected to the outer case, the first flexible pipe having at its base end a front end member having an opening of the tube, the second flexible pipe having at its end a rear end member having an opening of the tube and one of a check valve and a gas vent.

2. An endoscope sterilizing test pack comprising:
an inner case configured for insertion thereinto and removal therefrom of an indicator for checking a sterilization effect of sterilization treatment
a first tube having a first end and a second end, the first end being connected to the inner case via a first connection unit and being in communication with an inside of the inner case, the first connection unit having a first hole for communicating the inside of the inner case with the first tube;
a second tube having a third end and a fourth end, the third end being connected to the inner case via a second connection unit and being in communication with the inside of the inner case, the second connection unit having a second hole for communicating the inside of the inner case with the second tube;
an outer case housing the inner case and a part of the tubes; and
a tube housing unit in communication with the outer case and configured to house a remaining portion of the tubes inserted therethrough;
wherein the tube housing unit includes a single flexible pipe formed with a duct, the duct having the first tube and the second tube inserted thereinto.

3. The endoscope sterilizing test pack according to claim 2, wherein the second end and the fourth end are opened to an outside of the outer case.

4. The endoscope sterilizing test pack according to claim 2, wherein the outer case has a case body substantially hermetically housing the inner case and into which case body the inner case is inserted and removed.

5. The endoscope sterilizing test pack according to claim 2, wherein the tube housing unit further includes:
a first gas admission unit connected to the second end of the first tube, the first gas admission unit having a first gas admission port for admitting the sterilizing gas into the first tube,
a second gas admission unit connected to the fourth end of the second tube, the second gas admission unit having a second gas admission port for admitting the sterilizing gas into the second tube, and
an edge portion connected to an end of the flexible pipe, the edge portion shielding an air gap portion in the flexible pipe from the outside and holding the first gas admission unit and the second gas admission unit.

6. The endoscope sterilizing test pack according to claim 5, further comprising a check valve configured to discharge air in the periphery of the inner case and maintaining an air discharged state during the sterilization gas admission by taking advantage of a fact than inside of a sterilizer, into which the endoscope sterilizing test pack is placed, is brought into a negative pressure state prior to the sterilizing gas admission through the tube.

7. The endoscope sterilizing test pack according to claim 6, wherein peripheries of the inner case and the tube are maintained in a substantially vacuum atmosphere at least during sterilizing gas admission through the tube.

8. The endoscope sterilizing test pack according to claim 7, wherein the tube housing unit is configured so that heat transmission efficiency from an outer space to an outer surface of the remaining portion of the tubes, inserted thereinto, is equal to or lower than heat transmission efficiency from an outer space to a duct formed in an endoscope being sterilized.

9. The endoscope sterilizing test pack according to claim 5, further comprising a connection unit substantially hermetically coupling another end of the flexible pipe to the outer case.

10. The endoscope sterilizing test pack according to claim 9, further comprising a check valve discharging air in the periphery of the inner case and maintaining an air discharged state at the sterilizing gas admission by taking advantage of a fact that an inside of a sterilizer into which the endoscope sterilizing test pack is placed is brought into a negative pressure state prior to the sterilizing gas admission through the tube.

11. The endoscope sterilizing test pack according to claim 9, wherein a condition of the sterilization treatment is the same as a condition of the sterilization treatment of a duct of a predetermined endo scope being sterilized or the sterilization treatment requires a longer time than the sterilization treatment of the duct of the predetermined endoscope sterilized.

12. The endoscope sterilizing test pack according to claim 2, wherein the tube housing unit is formed by a bendable flexible pipe having flexibility, the endoscope sterilizing test pack further comprising a plurality of holders holding the tube housing unit spirally folded and extended by a predetermined length, wherein
each holder includes:
a plurality of insertion units configured with ducts for inserting the tube housing unit and
a plurality of connection units connecting the adjacent insertion units.

13. The endoscope sterilizing test pack according to claim 10, wherein the peripheries of the inner case and the tube are maintained in substantially vacuum atmosphere at least during sterilizing gas admission through the tube.

14. The endoscope sterilizing test pack according to claim 2, further comprising a check valve configured to discharge air in the periphery of the inner case and maintain an air discharged state during the sterilizing gas admission by utilizing that an inside of a sterilizer, into which the endoscope sterilizing test pack is placed, is subjected to a negative pressure state prior to the sterilizing gas admission through the tube.

15. The endoscope sterilizing test pack according to claim 14, wherein peripheries of the inner case and the tube are maintained in a substantially vacuum atmosphere at least during sterilizing gas admission through the tube.

16. The endoscope sterilizing test pack according to claim 15, wherein the tube housing unit is configured so that heat transmission efficiency from an outer space to an outer surface of the remaining portion of the tubes, inserted thereinto, is equal to or lower than heat transmission efficiency from an outer space to a duct formed in an endoscope being sterilized.

17. The endoscope sterilizing test pack according to claim 2, further comprising a connection unit substantially hermetically coupling another end of the flexible pipe to the outer case.

18. The endoscope sterilizing test pack according to claim 17, wherein a condition of the sterilization treatment is the same as a condition of the sterilization treatment of a duct of a predetermined endoscope being sterilized or the sterilization treatment requires a longer time than the sterilization treatment of the duct of the predetermined endoscope sterilized.

19. The endoscope sterilizing test pack according to claim 17, further comprising a check valve discharging air in the periphery of the inner case and maintaining an air discharged state at the sterilizing gas admission by taking advantage of a fact that an inside of a sterilizer into which the endoscope sterilizing test pack is placed is brought into a negative pressure state prior to the sterilizing gas admission through the tube.

20. The endoscope sterilizing test pack according to claim 19, wherein the peripheries of the inner case and the tube are maintained in substantially vacuum atmosphere at least during sterilizing gas admission through the tube.

* * * * *